United States Patent [19]

Bugaut et al.

[11] Patent Number: 4,888,025

[45] Date of Patent: Dec. 19, 1989

[54] COMPOUNDS WHICH CAN BE USED FOR HAIR DYEING, PROCESS FOR THEIR PREPARATION, DYEING COMPOSITIONS IN WHICH THEY ARE PRESENT AND CORRESPONDING HAIR-DYEING PROCESS

[75] Inventors: Andrée Bugaut, Boulogne; Alain Genet, Neuilly-Plaisance, both of France

[73] Assignee: L'Oreal, Paris, France

[21] Appl. No.: 742,240

[22] Filed: Jun. 7, 1985

Related U.S. Application Data

[63] Continuation of Ser. No. 459,964, Jan. 21, 1983, abandoned.

[30] Foreign Application Priority Data

Jan. 26, 1982 [LU] Luxembourg .............................. 83900
Sep. 27, 1982 [LU] Luxembourg .............................. 84391

[51] Int. Cl.$^4$ ................................................ A61K 7/13
[52] U.S. Cl. ............................................ 8/405; 8/406; 8/407; 8/408; 8/410; 8/411; 8/412; 8/414; 8/416; 8/428

[58] Field of Search .................... 8/405, 406, 407, 408, 8/410, 411, 412, 414, 416, 428

[56] References Cited

U.S. PATENT DOCUMENTS

| | | | |
|---|---|---|---|
| 3,982,012 | 9/1976 | Fauland et al. | 564/350 |
| 4,018,824 | 9/1977 | Tsukamoto et al. | 564/350 |
| 4,125,367 | 11/1978 | Bugaut et al. | 8/407 |
| 4,337,061 | 6/1982 | Bugaut et al. | 8/405 |

FOREIGN PATENT DOCUMENTS 0029964  6/1981  European Pat. Off. ................ 8/408

Primary Examiner—Douglas W. Robinson
Attorney, Agent, or Firm—Cushman, Darby & Cushman

[57] ABSTRACT

The present invention relates to new 1-(substituted phenoxy)-3-aminopropan-2-ol compounds in which the extra-nuclear amine group may or may not be substituted, and to the process for their preparation. The invention also relates to hair-dyeing compositions containing these new compounds and to a dyeing process using the said compositions.

11 Claims, No Drawings

COMPOUNDS WHICH CAN BE USED FOR HAIR DYEING, PROCESS FOR THEIR PREPARATION, DYEING COMPOSITIONS IN WHICH THEY ARE PRESENT AND CORRESPONDING HAIR-DYEING PROCESS

This is a continuation of application Ser. No. 459,964, filed Jan. 21, 1983, now abandoned.

The present invention relates to new 1-(substituted phenoxy)-3-aminopropan-2-ol compounds in which the extra-nuclear amine group may or may not be substituted, and to the process for their preparation. The invention also relates to hair-dyeing compositions containing these new compounds and to a dyeing process using the said compositions.

Summary of the Invention

The object of the invention is to propose a new class of compounds which can be used in hair dyes to give strong colourations which are stable to light and have a good fastness to weather and washing. A further object of the invention is to propose a new category of compounds having a good degree of harmlessness and satisfactory characteristics from the point of view of mutagenesis.

The present invention relates to a new chemical compound of the formula (I) (or a corresponding acid salt)

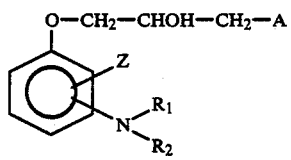  (I)

in which formula:
Z represents $NO_2$ or $NH_2$;
A denotes NY or the group

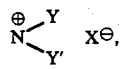 $X^\ominus$,

Y representing two identical or different lower alkyl or lower hydroxyalkyl substituent groups having at most 4 carbon atoms, these two groups optionally forming a morpholine or piperidine heterocyclic ring with the nitrogen atom to which they are attached, and it also being possible for one or both of the substituents of which Y is composed to represent hydrogen, only if A denotes NY, Y' representing a lower alkyl substituent group having at most 4 carbon atoms, and X representing an anion; and $R_1$ and $R_2$ are identical or different and represent a hydrogen atom or a lower alkyl or hydroxyalkyl radical having at most 4 carbon atoms, with the proviso that if A denotes NY, 1°) if Z is in the 4-position on the benzene nucleus and if $NR_1R_2$ is in the 2-position, $R_1$ and $R_2$ both representing a hydrogen atom, one of the two substituents of which Y is composed does not represent an ethyl group if the other substituent represents a hydrogen atom, and the two substituents of which Y is composed do not form a morpholine or piperidine heterocyclic ring with the nitrogen atom to which they are attached, and 2°) if one of the two substituents of which Y is composed denotes a hydrogen atom or an alkyl group and the other denotes an alkyl group, Z cannot be located in the 3-position and $NR_1R_2$ in the 2-position, $R_1$ denoting a hydrogen atom and $R_2$ denoting a hydrogen atom or an alkyl group.

X can advantageously be a halogen, in particular chlorine.

The present invention also relates to a process for the preparation of a chemical compound of the formula (I) (or a corresponding acid salt) in which:

Z represents $NO_2$ or $NH_2$;

A denotes NY, Y representing two identical or different lower alkyl or lower hydroxyalkyl substituent groups having at most 4 carbon atoms, these two groups optionally forming a morpholine or piperidine heterocyclic ring with the nitrogen atom to which they are attached, and it also being possible for one or both of the substituents of which Y is composed to represent hydrogen; and $R_1$ and $R_2$ represent hydrogen atoms, with the proviso that if Z is in the 4-position on the benzene nucleus and if $NR_1R_2$ is in the 2-position, one of the two substituents of which Y is composed does not represent an ethyl group if the other substituent represents a hydrogen atom, and the two substituents of which Y is composed do not form a morpholine or piperidine ring with the nitrogen atom to which they are attached; the process comprising the following steps:

(a) epichlorohydrin is reacted with the known compound of the formula (II)

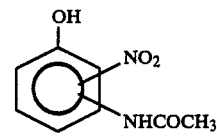  (II)

to give the compound of the formula (III)

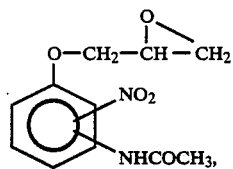  (III)

(b) an amine of the formula HNY, in which Y has the meaning indicated above, is reacted with the compound of the formula (III) to give the compound of the formula (IV)

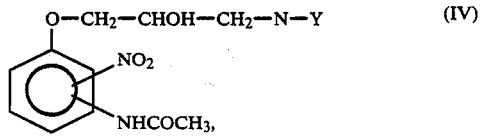  (IV)

(c) a strong acid, such as hydrochloric acid, is reacted with the compound of the formula (IV) to give the compound of the formula (V)

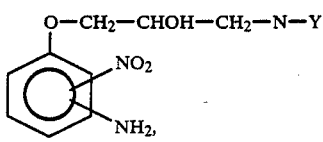

(d) and, if appropriate, to obtain the compound of the formula (I) in which Z represents $NH_2$, reduction is carried out either, for example, by means of zinc powder in an alcoholic medium in the presence of ammonium chloride, or by means of catalytic hydrogenation, it being possible for palladium-on-charcoal to be used as the catalyst, and this makes it possible to obtain the compound of the formula (VI)

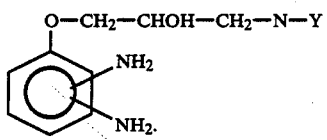

The present invention also relates to a process for the preparation of a chemical compound of the formula (I) (or corresponding acid salt) in which:
Z represents $NO_2$ or $NH_2$;
A denotes NY, Y representing two identical or different lower alkyl or lower hydroxyalkyl substituent groups having at most 4 carbon atoms, these two groups optionally forming a morpholine or piperidine heterocyclic ring with the nitrogen atom to which they are attached, and it also being possible for one or both of the substituents of which Y is composed to represent hydrogen; and
$R_1$ and $R_2$ are identical or different and represent a hydrogen atom or a lower alkyl or hydroxyalkyl radical having at most 4 carbon atoms, the case in which $R_1=R_2=H$ being excluded, in which process the compound of the formula (VII)

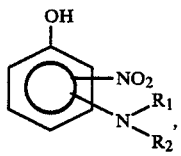

in which formula $R_1$ and $R_2$ have the meanings indicated above, is used as the starting material, and the reactions involved in steps (a) and (b) mentioned above are carried out successively to give a product of the formula (VIII)

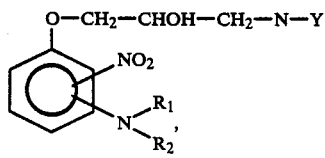

in which Y, $R_1$ and $R_2$ have the meanings indicated above, and if it is desired to obtain a compound of the formula (I) (or a corresponding acid salt) in which Z represents $NH_2$, A denoting NY, the compound of the formula (VIII) is subjected to reduction as indicated in step (d) mentioned above. As a variant, if neither of the substituents of which Y is composed represents a hydrogen atom, it is possible to use a process of preparation which starts from a compound of the formula (II), to carry out steps (a), (b), (c) and (d) and then to introduce a substituent into one of the nuclear amine groups of the compound of the formula (VI), for example by introducing a substituent into the corresponding arylsulphonamide and subjecting this substituted arylsulphonamide to acid hydrolysis.

The present invention also relates to a process for the preparation of a compound of the formula (I) in which:
Z denotes $NO_2$ or $NH_2$;
A denotes

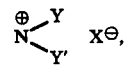

Y representing two identical or different lower alkyl or lower hydroxyalkyl substituent groups having at most 4 carbon atoms, these two groups optionally forming a morpholine or piperidine heterocyclic ring with the nitrogen atom to which they are attached, Y' representing a lower alkyl substituent group having at most 4 carbon atoms, and X representing an anion; and
$R_1$ and $R_2$ are identical or different and represent a hydrogen atom or a lower alkyl or hydroxyalkyl radical having at most 4 carbon atoms; in which process the nuclear amine group (or groups) of the corresponding tertiary compound is (or are) protected by acetylation, this being followed by reaction with a quaternising agent. Subsequently, the product is deacetylated by reaction with an acid and, if appropriate, the quaternisation anion can be changed at the same time.

In the case where Z represents a nitro group, the compounds of the formula (I) are direct dyestuffs which can be used for dyeing keratin fibres, and in particular hair. It has been found that these compounds have the advantage of good solubility in the solvents generally used in hair dyeing, and this enables them to be used at a sufficiently high concentration to give the keratin fibre a strong colouration with a good uniformity. The dyeing obtained has a good stability to light and weather. Furthermore, the use of these compounds in hair dyeing is characterised by a good degree of harmlessness. The invention thus also relates to a dyeing composition for keratin fibres, and in particular for hair, which composition contains, in an appropriate carrier, at least one compound of the formula (I) (or a corresponding acid salt) in which:
Z represents a nitro group;
A denotes NY or

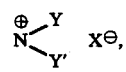

Y representing two identical or different lower alkyl or lower hydroxyalkyl substituent groups having at most 4 carbon atoms, these two groups optionally forming a morpholine or piperidine heterocyclic ring with the nitrogen atom to which they are attached, and it also being possible for one or both of the substituents of which Y is composed to represent hydrogen, only if A denotes NY, Y' representing a lower alkyl substituent group having at most 4 carbon atoms, and X representing an anion; and $R_1$ and $R_2$ are identical or different and represent a hydrogen atom or a lower alkyl or hydroxyalkyl radical having at most 4 carbon atoms. In a preferred embodiment, the dyeing composition according to the invention contains from 0.001% to 4% by weight of at least one compound of the formula (I).

In the case where Z represents an $NH_2$ group, the compounds of the formula (I) are either oxidation bases, in the case of para-diamines or ortho-diamines, or couplers intended to be used in association with oxidation bases, in the case of meta-diamines.

If the compound of the formula (I) is an oxidation base, the invention also relates to a dyeing composition for keratin fibres, in particular for hair, which composition contains, in an appropriate carrier, at least one compound of the formula (I) (or a corresponding acid salt), in which formula:

Z represents an $NH_2$ group;
A denotes NY or

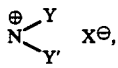 $X^\ominus$,

Y representing two identical or different lower alkyl or lower hydroxyalkyl substituent groups having at most 4 carbon atoms, these two groups optionally forming a morpholine or piperidine heterocyclic ring with the nitrogen atom to which they are attached, and it also being possible for one or both of the substituents of which Y is composed to represent hydrogen, only if A denotes NY, Y' representing a lower alkyl substituent group having at most 4 carbon atoms, and X representing an anion; and $R_1$ and $R_2$ are identical or different and represent a hydrogen atom or a lower alkyl or hydroxyalkyl radical having at most 4 carbon atoms. In a preferred embodiment, the compound of the formula (I) is used in a proportion of between 0.001% and 4% by weight, relative to the total weight of the composition.

In the case where the compound of the formula (I) is a meta-phenylenediamine, the invention also relates to a dyeing composition for keratin fibres, and in particular for hair, containing, in an appropriate carrier, at least one oxidation base, which composition also contains at least one compound of the formula (I) (or a corresponding acid salt), in which formula:

Z represents an $NH_2$ group;
A denotes NY or

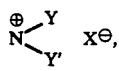 $X^\ominus$,

Y representing two identical or different lower alkyl or lower hydroxyalkyl substituent groups having at most 4 carbon atoms, these two groups optionally forming a morpholine or piperidine heterocyclic ring with the nitrogen atom to which they are attached, and it also being possible for one or both of the substituents of which Y is composed to represent hydrogen, only if A denotes NY, Y' representing a lower alkyl substituent group having at most 4 carbon atoms, and X representing an anion; and $R_1$ and $R_2$ are identical or different and represent a hydrogen atom or a lower alkyl or hydroxyalkyl radical having at most 4 carbon atoms, with the proviso that if A denotes NY, if Z is in the 4-position on the benzene nucleus and if $NR_1R_2$ is in the 2-position, $R_1$ and $R_2$ both representing a hydrogen atom, one of the two substituents of which Y is composed does not represent an ethyl group if the other substituent represents a hydrogen atom, and the two substituents of which Y is composed do not form a morpholine or piperidine heterocyclic ring with the nitrogen atom to which they are attached. The compound of the formula (I) is preferably used in a proportion of between 0.001% and 2.5% by weight, relative to the total weight of the composition.

The dyeing compositions according to the invention can comprise, in addition to the compounds of the formula (I), oxidation bases consisting of:

A - Para-phenylenediamines of the general formula (IX)

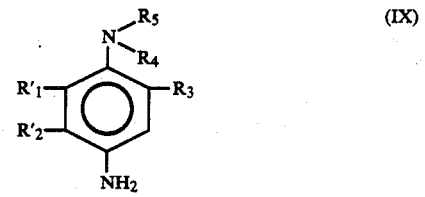

or the corresponding acid salts, in which formula $R'_1$, $R'_2$ and $R_3$ are identical or different and represent a hydrogen atom, an alkyl radical having from 1 to 4 carbon atoms, an alkoxy radical having 1 or 2 carbon atoms or a halogen atom, and $R_4$ and $R_5$ are identical or different and represent a hydrogen atom, an alkyl or hydroxyalkyl radical, an alkoxyalkyl radical in which the alkoxy group contains 1 or 2 carbon atoms, or a carbamylalkyl, alkylsulphonamidoalkyl, acetylaminoalkyl, ureidoalkyl, carbethoxyaminoalkyl, aminoalkyl, monoalkylaminoalkyl, dialkylaminoalkyl, piperidinoalkyl or morpholinoalkyl radical, the alkyl groups in $R_4$ and $R_5$ having from 1 to 4 carbon atoms, or alternatively $R_4$ and $R_5$ form a piperidino or morpholino group together with the nitrogen atom to which they are attached, with the proviso that $R'_1$ and $R_3$ represent a hydrogen atom if $R_4$ and $R_5$ do not represent a hydrogen atom.

B - Para-aminophenols of the general formula (X)

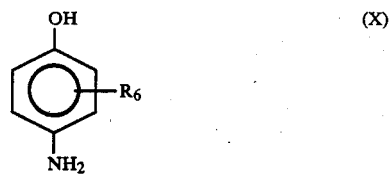

or the corresponding acid salts, in which formula $R_6$ represents a hydrogen atom, an alkyl radical containing from 1 to 4 carbon atoms or a halogen atom such as, for example, chlorine or bromine.

C - Heterocyclic bases such as 2,5-diaminopyridine, 3-methyl-7-aminobenzomorpholine and 5-aminoindole.

In addition to the compounds of the formula (I), the dyeing compositions according to the invention can contain the following products, taken in isolation or in combination:

(1) if the composition contains at least one oxidation base: at least one coupler taken from the group comprising resorcinol, pyrocatechol, 2-methylresorcinol, 2-ethylresorcinol, meta-aminophenol, 2-methyl-5-aminophenol, 2-methyl-5-N-(β-hydroxyethyl)-aminophenol, 6-hydroxybenzomorpholine, 2,6-dimethyl-3-acetylaminophenol, 2-methyl-5-carbethoxyaminophenol, 2-methoxy-5-carbethoxyaminophenol, 2-methyl-5-ureidophenol, 2,4-diaminophenoxyethanol, 2,4-diaminoanisole, 2,6-dimethyl-meta-phenylenediamine, 2-amino-4-N-methylaminophenoxyethanol, 2,4-diaminophenyl β-methoxyethyl ether, 2,4-diaminophenyl β-mesylaminoethyl ether, 2-N-carbamylmethylamino-4-aminoanisole, 3-amino-4-methoxyphenol, α-naphthol, 2,6-diaminopyridine, 3,5-diamino-2,6-dimethoxypyridine, 1-phenyl-3-methylpyrazol-5-one and 2-amino-4-N-(β-hydroxyethyl)-aminophenyl β-hydroxypropyl ether;

(2) ortho-phenylenediamines and ortho-aminophenols optionally containing substituents on the nucleus or on the amine groups, or ortho-diphenol, it being possible, by means of complex oxidation mechanisms, for these products to lead to new coloured compounds, either by cyclisation with themselves or by reaction with para-phenylenediamines;

(3) dyestuff precursors of the benzene series, containing, on the nucleus, at least three substituents chosen from the group comprising hydroxyl, methoxy or amino groups, such as 2,6-diaminohydroquinone dihydrochloride, 2,6-diamino-4-N,N-bis-(ethyl)-aminophenol trihydrochloride, 2,4-diaminophenol dihydrochloride, 1,2,4-trihydroxybenzene, 2,3,5-trihydroxytoluene or 4-methoxy-2-amino-N-(β-hydroxyethyl)-aniline;

(4) quinone dyestuffs such as 2-hydroxy-1,4-naphthoquinone, 5-hydroxy-1,4-naphthoquinone and 2-[4'-(N,N-dihydroxyethylamino)-anilino]-5-N'-(β-hydroxyethyl)-amino-1,4-benzoquinone;

(5) indoanilines, indophenols or indamines, or their leuco derivatives, such as 4,4'-dihydroxy-2-amino-5-methyldiphenylamine, 4,4'-dihydroxy-2-N-(β-hydroxyethyl)-amino-5-methyl-2'-chlorodiphenylamine, 2,4'-diamino-4-hydroxy-5-methyldiphenylamine, 2,4-dihydroxy-4'-N-(β-methoxyethyl)aminodiphenylamine and 2,4-dihydroxy-5-methyl-4'-N-(β-methoxyethyl)-aminodiphenylamine;

(6) direct dyestuffs chosen from the class of the azo dyestuffs, the anthraquinone dyestuffs and the nitro dyestuffs of the benzene series, such as 2-amino-3-nitrophenol, 1-amino-2-nitro-4-N-(β-hydroxyethyl)-amino-5-methylbenzene, 1-N,N-bis-(β-hydroxyethyl)-amino-3-nitro-4-N'-methylaminobenzene, 1-N-methyl-N-(β-hydroxyethyl)amino-3-nitro-4-N'-(β-hydroxyethyl)-aminobenzene, 1-N-methyl-N-(β-hydroxyethyl)-amino-3-nitro-4-N'-methylaminobenzene, 3-nitro-4-N-(β-hydroxyethyl)-aminoanisole, 3-nitro-4-N-(β-hydroxyethyl)-aminophenol, 3-nitro-4-aminophenoxyethanol, 3-nitro-4-N-methylaminophenoxyethanol, 3-N-methylamino-4-nitrophenoxyethanol, 3-nitro-4-N-(β-aminoethyl)-aminophenoxyethanol, 2-N-(β-hydroxyethyl)-amino-5-nitroanisole and 1,4,5,8-tetraaminoanthraquinone; and (7) various customary adjuvants such as water, penetrating agents, surface-active agents, thickeners, antioxidants, alkalising or acidifying agents, perfumes, sequestering agents, film-forming products and treating agents.

The pH of the dyeing compositions according to the invention is between 5 and 11.5. Amongst the alkalising agents which can be used, there may be mentioned ammonia, alkylamines such as ethylamine or triethylamine, alkanolamines such as mono-, di- or tri-ethanolamine, alkylalkanolamines such as methyldiethanolamine, the hydroxides of sodium or potassium and the carbonates of sodium, potassium or ammonium. Amongst the acidifying agents which can be used, there may be mentioned lactic acid, acetic acid, tartaric acid and phosphoric acid.

Water-soluble anionic, cationic, non-ionic or amphoteric surface-active agents, or a mixture thereof, can also be added to the composition according to the invention. Amongst the surface-active agents which can be used in particular, there may be mentioned alkylbenzenesulphonates, alkylnaphthalenesulphonates, fatty alcohol sulphates, ether-sulphates and sulphonates, quaternary ammonium salts such as trimethylcetylammonium bromide and cetylpyridinium bromide, fatty acid diethanolamides or polyoxyethyleneated or polyglycerolated acids, alcohols or alkylphenols. Preferably, the surface-active agents are present in the composition according to the invention in a proportion of between 0.5 and 55% by weight and advantageously of between 4 and 40% by weight, relative to the total weight of the composition.

Organic solvents can also be added to the composition according to the invention, and examples of these which may advantageously be mentioned are ethanol, isopropanol, glycerol, glycols and their ethers, such as 2-butoxyethanol, ethylene glycol, propylene glycol, and diethylene glycol monoethyl ether and monomethyl ether, and similar solvents. The solvents can advantageously be present in the composition in a proportion ranging from 1 to 40% by weight and preferably of between 5 and 30% by weight, relative to the total weight of the composition.

The thickening products which can be added to the composition according to the invention can advantageously be taken from the group comprising sodium alginate, gum arabic, cellulose derivatives such as methylcellulose, hydroxyethylcellulose, hydroxypropylmethylcellulose and the sodium salt of carboxymethylcellulose, and acrylic acid polymers; it is also possible to use inorganic thickeners such as bentonite. Preferably, the thickeners are present in a proportion of between 0.5 and 5% by weight, relative to the total weight of the composition, and advantageously of between 0.5 and 3% by weight.

The antioxidants which can be added to the composition according to the invention can advantageously be taken from the group comprising sodium sulphite, thioglycolic acid, mercaptosuccinic acid, sodium bisulphite, ascorbic acid and hydroquinone. These antioxidants can be present in the composition in a proportion of between 0.05 and 1.5% by weight, relative to the total weight of the composition.

If the dyeing composition according to the invention contains at least one oxidation base, it contains, at the time of use, oxidising agents such as hydrogen peroxide, urea peroxide or per-salts such as ammonium persulphate.

The dyeing composition according to the invention can be present in the form of a liquid, a cream, a gel or an aerosol or in any other form suitable for dyeing keratin fibres.

The present invention also relates to a new hairdyeing process, characterised in that the dyeing composition defined above is left to act on the hair for an application time varying between 10 and 45 minutes, and in that the hair is rinsed, optionally washed and rinsed again, and dried.

In the case where the dyeing composition used contains at least one oxidation base, the abovementioned process includes an initial stage in which a sufficient amount of oxidising agents is mixed with the said composition at the time of use.

To provide a clearer understanding of the object of the invention, several embodiments thereof will now be described by way of purely illustrative and non-limiting examples.

EXAMPLE 1

Preparation of 1-(3′-nitro-4′-aminophenoxy)-3-N,N-diethylaminopropan-2-ol

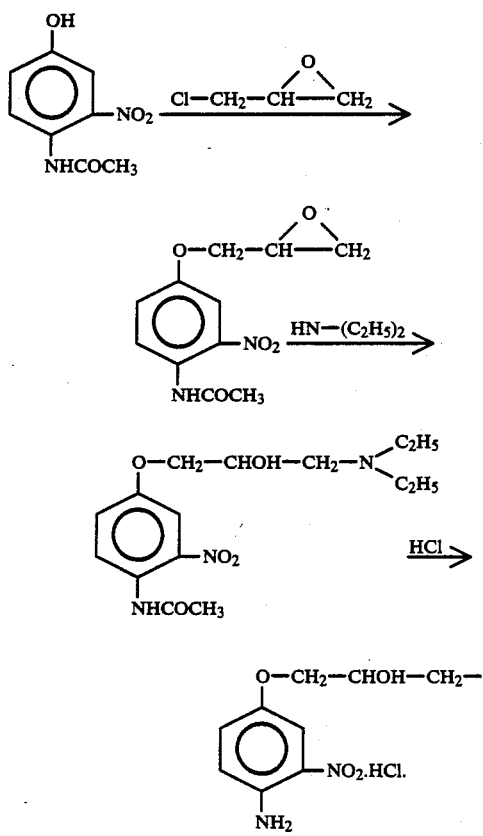

First step

Preparation of 1-(3′-nitro-4′-acetylaminophenoxy)-2,3-epoxypropane 150 ml of epichlorohydrin are added, at ambient temperature, to a solution of 0.376 mol (73.7 g) of 3-nitro-4-acetylaminophenol in 375 ml of 1.1N sodium hydroxide solution. The reaction medium is left to stand at ambient temperature for 48 hours, with thorough stirring, and the expected product which has precipitated is then filtered off. After drying in vacuo and recrystallisation from benzene, this product melts at 123° C.

The product obtained corresponds to the following analysis results:

| Analysis | Calculated for $C_{11}H_{12}N_2O_5$ | Found |
|---|---|---|
| C % | 52.38 | 52.32 |
| H % | 4.80 | 4.77 |
| N % | 11.11 | 11.06 |
| O % | 31.72 | 31.57 |

Second step

Preparation of 1-(3′-nitro-4′-acetylaminophenoxy)-3-N,N-diethylaminopropan-2-ol 0.2 mol (50.4 g) of 1-(3′-nitro-4′-acetylaminophenoxy)-2,3-epoxypropane is heated for 3 hours under reflux in 146 g of diethylamine and 50 ml of absolute alcohol. The diethylamine and the alcohol are driven off in vacuo. The residual oil crystallises slowly. After recrystallisation from cyclohexane, 58 g of the expected product, which melts at 77° C., are obtained.

The product obtained corresponds to the following analysis results:

| Analysis | Calculated for $C_{15}H_{23}N_3O_5$ | Found |
|---|---|---|
| C % | 55.37 | 55.40 |
| H % | 7.13 | 7.18 |
| N % | 12.92 | 12.86 |
| O % | 24.59 | 24.78 |

Third step:

Preparation of 1-(3′-nitro-4′-aminophenoxy)-3-N,N-diethylaminopropan-2-ol hydrochloride 0.152 mol (49.7 g) of 1-(3′-nitro-4′-acetylaminophenoxy)-3-N,N-diethylaminopropan-2-ol is heated for 30 minutes, in a boiling water-bath, in 100 ml of hydrochloric acid (specific gravity=1.18). After the addition of ammonia to the reaction medium so as to give a pH of 6, the 1-(3′-nitro-4′-aminophenoxy)-3-N,N-diethylaminopropan-2-ol monohydrochloride crystallises. It is filtered off, washed with a small amount of 80° strength alcohol, recrystallised from a mixture of water and ethanol and dried in vacuo. It melts at 178° C.

The product obtained corresponds to the following analysis results:

| Analysis | Calculated for $C_{13}H_{21}N_3O_4 \cdot HCl$ | Found |
|---|---|---|
| C % | 48.82 | 48.65 |
| H % | 6.93 | 6.90 |
| N % | 13.14 | 12.90 |
| O % | 20.01 | 20.17 |
| Cl % | 11.09 | 10.96 |

EXAMPLE 2

Preparation of
1-(3'-nitro-4'-aminophenoxy)-3-N-propylaminopropan-2-ol monohydrochloride

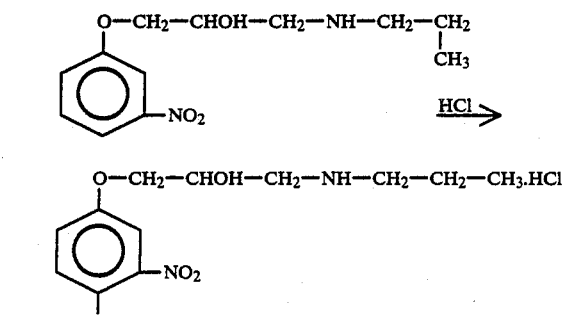

First step

Preparation of
1-(3'-nitro-4'-acetylaminophenoxy)-3-N-propylaminopropan-2-ol 0.02 mol (5.0 g) of 1-(3'-nitro-4'-acetylaminophenoxy)-2,3-epoxypropane, obtained according to the first step of Example 1, is introduced into 25 ml of N-propylamine and the mixture is then heated for 3 hours at 45° C. The reaction medium is subsequently poured into 100 g of iced water, and the expected product which has precipitated is then filtered off and washed with water. After drying in vacuo and recrystallisation from a mixture of benzene and ethyl acetate, the product melts at 146° C.

The product obtained corresponds to the following analysis results:

| Analysis | Calculated for $C_{14}H_{21}N_3O_5$ | Found |
|---|---|---|
| C % | 54.01 | 54.00 |
| H % | 6.80 | 6.86 |
| N % | 13.50 | 13.36 |
| O % | 25.70 | 25.88 |

Second step

Preparation of
1-(3'-nitro-4'-aminophenoxy)-3-N-propylaminopropan-2-ol monohydrochloride 0.008 mol (2.5 g) of 1-(3'-nitro-4'-acetylaminophenoxy)-3-N-propylaminopropan-2-ol is heated for 30 minutes, in a boiling water-bath, in 7 ml of hydrochloric acid (specific gravity=1.18), with stirring. The cooled reaction mixture is treated with 22°Be ammonia solution up to a pH of 5. The monohydrochloride of the expected product precipitates. It is filtered off, washed with a small amount of 80° strength alcohol and then recrystallised from a mixture of water and ethanol. It melts at 224° C.

The product obtained corresponds to the following analysis results:

| Analysis | Calculated for $C_{12}H_{19}N_3O_4.HCl$ | Found |
|---|---|---|
| C % | 47.14 | 47.24 |
| H % | 6.59 | 6.57 |
| N % | 13.74 | 13.75 |
| O % | 20.93 | 20.76 |
| Cl % | 11.60 | 11.55 |

EXAMPLE 3

Preparation of
1-(3'-nitro-4'-aminophenoxy)-3-aminopropan-2-ol

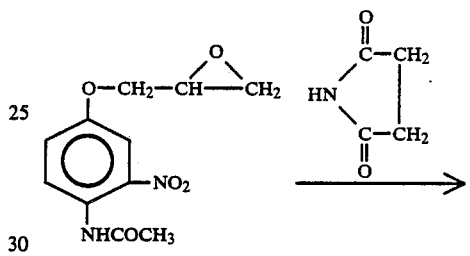

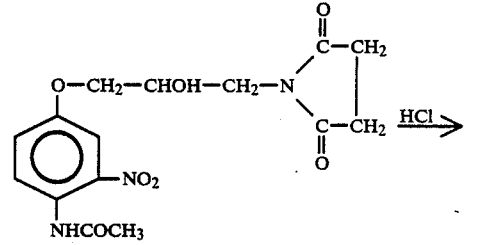

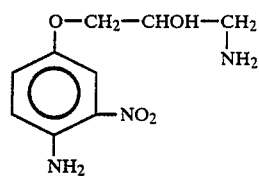

First step

Preparation of
1-(3'-nitro-4'-acetylaminophenoxy)-3-succinimido-3-propan-2-ol 50.4 g (0.2 mol) of 1-(3'-nitro-4'-acetylaminophenoxy)-2,3-epoxypropane (prepared according to the first step of Example 1) are introduced into 150 ml of absolute ethanol to which 12 drops of pyridine have been added. 0.24 mol (23.7 g) of succinimide is added. The mixture is heated under reflux for 5 hours 30 minutes. On cooling, the expected product crystallises. It is filtered off and washed with a small amount of alcohol. After recrystallisation from alcohol and drying in vacuo, it melts at 154° C.

The product obtained corresponds to the following analysis results:

| Analysis | Calculated for $C_{15}H_{17}N_3O_7$ | Found |
|---|---|---|
| C % | 51.28 | 51.34 |
| H % | 4.88 | 4.95 |
| N % | 11.96 | 11.86 |
| O % | 31.83 | 31.84 |

Second step

Preparation of 1-(3'-nitro-4'-aminophenoxy)-3-aminopropan-2-ol 50.9 g (0.145 mol) of the succinimido derivative obtained according to the first step are introduced into 100 ml of 96° strength alcohol to which 250 ml of hydrochloric acid (specific gravity=1.18) have been added. After 14 hours under reflux, the cooled reaction medium is treated with acetone. The expected product precipitates in the form of the hydrochloride. This hydrochloride is taken up in 70 ml of water. By rendering the aqueous solution alkaline with 10 N sodium hydroxide solution, the 1-(3'-nitro-4'-aminophenoxy)-3-aminopropan-2-ol is precipitated in the form of an oil, which crystallises rapidly. After recrystallisation from alcohol, the product melts at 124° C.

The product obtained corresponds to the following analysis results:

| Analysis | Calculated for $C_9H_{13}N_3O_4$ | Found |
|---|---|---|
| C % | 47.57 | 47.54 |
| H % | 5.77 | 5.73 |
| N % | 18.49 | 18.36 |
| O % | 28.17 | 28.18 |

EXAMPLE 4

Preparation of 1-(2'-amino-4'-nitrophenoxy)-3-aminopropan-2-ol

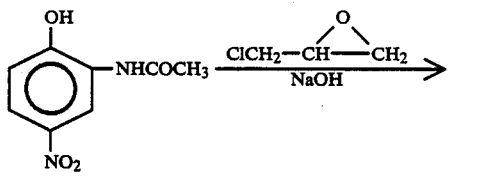

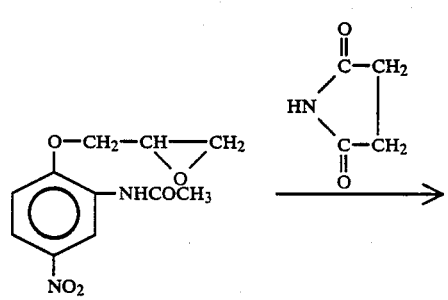

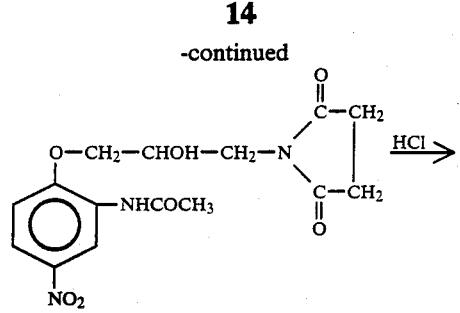

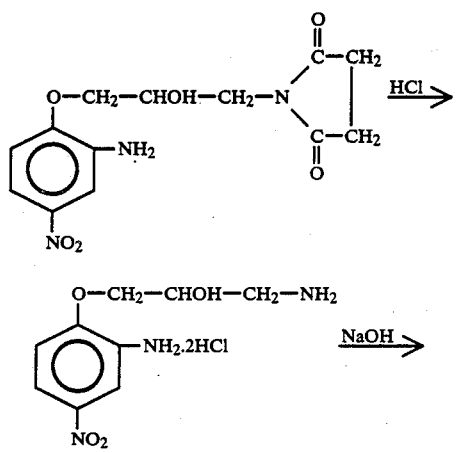

First step

Preparation of 1-(2'-acetylamino-4'-nitrophenoxy)-2,3-epoxypropane 1.6 liters of epichlorohydrin are added to a solution of 2 mols (392 g) of 2-acetylamino-4-nitrophenol in two liters of 1.1 N sodium hydroxide solution, and the reaction medium is left to stand for 96 hours at 20° C., with thorough stirring. 282 g of the expected product which has precipitated are filtered off and washed with water. This product contains about 20% of a by-product, namely 1,3-bis-(2'-acetylamino-4'-nitrophenoxy)-propan-2-ol (melting at 233° C.), which results from the condensation of one molecule of epichlorohydrin with two mols of 2-acetylamino-4-nitrophenol. However, it will be used as such for the second step of the synthesis, the by-product being very readily removed at this stage.

Second step

Preparation of 1-(2'-acetylamino-4'-nitrophenoxy)-3-succinimidopropan-2-ol 100 g of the crude product obtained in the previous step are introduced into 500 ml of 95° strength ethanol. 0.52 mol (51.5 g) of succinimide and 2.5 ml of pyridine are added and the mixture is heated under reflux for 2 hours, with stirring. The alcoholic solution is filtered at the boil to isolate the expected product, which is insoluble in hot alcohol. This gives 60 g of virtually pure 1-(2'-acetylamino-4'-nitrophenoxy)-3-succinimidopropan-2-ol. After recrystallisation from alcohol, this product melts at 184° C.

The product obtained corresponds to the following analysis results:

| Analysis | Calculated for $C_{15}H_{17}N_3O_7$ | Found |
|---|---|---|
| C % | 51.28 | 51.15 |
| H % | 4.84 | 4.87 |
| N % | 11.96 | 11.86 |
| O % | 31.91 | 32.15 |

The mother liquors from the reaction medium contain a small amount of succinimido derivative together with 1,3-bis-(2'-acetylamino-4'-nitrophenoxy)-propan-2-ol, which has thus been removed.

Third step

Preparation of 1-(2'-amino-4'-nitrophenoxy)-3-succinimidopropan-2-ol 2 g (0.0057 mol) of the 1-(2'-acetylamino-4'-nitrophenoxy)-3-succinimidopropan-2-ol obtained in the second step are heated for one hour, in a boiling water-bath, in 10 ml of hydrochloric acid (specific gravity=1.18), with stirring. After the reaction medium has been cooled, diluted and rendered alkaline, the expected product precipitates. It is filtered off, washed with water and recrystallised from ethanol. It melts at 200° C.

The product obtained corresponds to the following analysis results:

| Analysis | Calculated for $C_{13}H_{15}N_3O_6$ | Found |
|---|---|---|
| C % | 50.48 | 50.47 |
| H % | 4.85 | 4.87 |
| N % | 13.59 | 13.58 |
| O % | 31.07 | 30.94 |

Fourth step

Preparation of 1-(2'-amino-4'-nitrophenoxy)-3-aminopropan-2-ol 7.9 g (0.0256 mol) of the succinimido derivative prepared in the previous step are heated for 8 hours in 40 ml of hydrochloric acid (specific gravity=1.18) under reflux, with stirring. After the reaction medium has cooled, the expected product, which has crystallised in the form of the dihydrochloride, is filtered off. This dihydrochloride is dissolved in 175 ml of water and the pH is brought to 9 with sodium hydroxide solution. The expected product which has precipitated is filtered off. After washing with water and recrystallisation from alcohol, the product melts at 159° C.

The product obtained corresponds to the following analysis results:

| Analysis | Calculated for $C_9H_{13}N_3O_4$ | Found |
|---|---|---|
| C % | 47.58 | 47.57 |
| H % | 5.73 | 5.75 |
| N % | 18.50 | 18.56 |
| O % | 28.19 | 28.16 |

EXAMPLE 5

Preparation of 1-(2'-amino-5'-nitrophenoxy)-3-aminopropan-2-ol

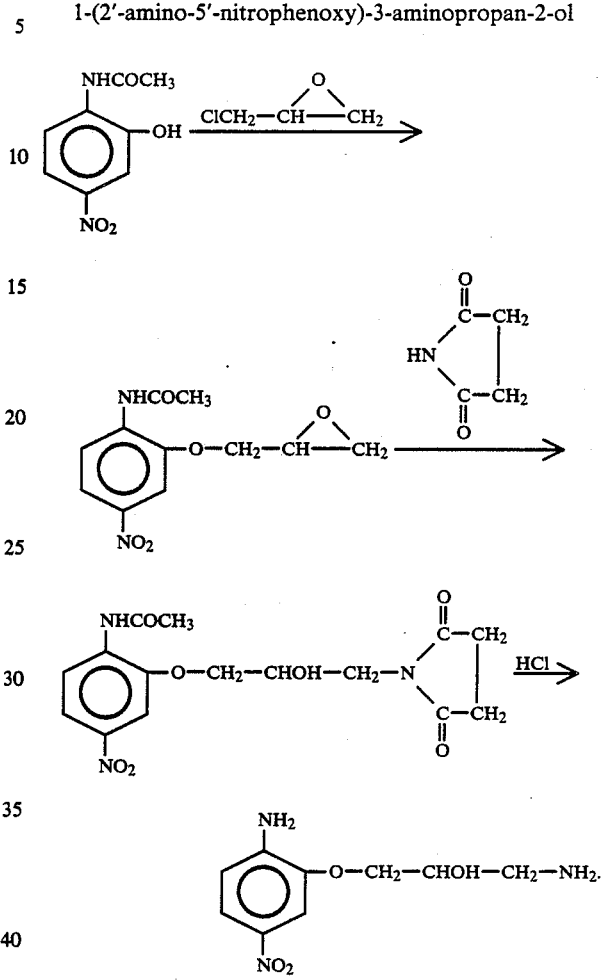

First step

Preparation of 1-(2'-acetylamino-5'-nitrophenoxy)-2,3-epoxypropane 0.376 mol (73.7 g) of 2-acetylamino-5-nitrophenol is dissolved in 375 ml of 1.1 N sodium hydroxide solution, and 300 ml of epichlorohydrin are then added. The reaction medium is left to stand for 96 hours at 20° C., with thorough stirring, and the expected product which has precipitated is then filtered off and washed with water. After recrystallisation from ethanol and drying in vacuo, it melts at 164° C.

The product obtained corresponds to the following analysis results:

| Analysis | Calculated for $C_{11}H_{12}N_2O_5$ | Found |
|---|---|---|
| C % | 52.38 | 52.29 |
| H % | 4.80 | 4.83 |
| N % | 11.11 | 11.20 |
| O % | 31.72 | 31.86 |

Second step

Preparation of 1-(2'-acetylamino-5'-nitrophenoxy)-3-succinimidopropan-2-ol 0.072 mol (18.2 g) of 1-(2'-acetylamino-5'-nitrophenoxy)-2,3-epoxypropane is introduced into 60 ml of absolute ethanol to which 6 drops of pyridine have been added. 0.087 mol (8.6 g) of succinimide is added and the mixture is then heated under reflux for 5 hours. After cooling, 150 ml of water are added and the alcohol is driven off in vacuo. The expected product, which is obtained initially in the form of a water-insoluble oil, crystallises slowly. It is filtered off and recrystallised from 96° strength alcohol. After drying, it melts at 157° C.

The product obtained corresponds to the following analysis results:

| Analysis | Calculated for $C_{15}H_{17}N_3O_7$ | Found |
|---|---|---|
| C % | 51.28 | 51.30 |
| H % | 4.88 | 4.94 |
| N % | 11.96 | 11.89 |
| O % | 31.88 | 32.07 |

Third step

Preparation of 1-(2'-amino-5'-nitrophenoxy)-3-aminopropan-2-ol 7.0 g (0.02 mol) of the succinimido derivative obtained in the second step are heated under reflux for 14 hours in 14 ml of 96° strength alcohol to which 38 ml of hydrochloric acid (specific gravity=1.18) have been added. The reaction medium is then cooled and treated with acetone in order to precipitate the expected product in the form of the hydrochloride. This hydrochloride is filtered off and then dissolved in 12 ml of water. By rendering the aqueous solution alkaline with 10 N sodium hydroxide solution, the 1-(2'-amino-5'-nitrophenoxy)-3-aminopropan-2-ol is precipitated in the form of an oil, which crystallises rapidly. The product is filtered off, washed with water and recrystallised from ethanol. It melts at 141° C.

The product obtained corresponds to the following analysis results:

| Analysis | Calculated for $C_9H_{13}N_3O_4$ | Found |
|---|---|---|
| C % | 47.57 | 47.58 |
| H % | 5.77 | 5.76 |
| N % | 18.49 | 18.62 |
| O % | 28.17 | 28.28 |

EXAMPLE 6

Preparation of 1-(2'-amino-5'-nitrophenoxy)-3-N-(β-hydroxyethyl)-aminopropan-2-ol

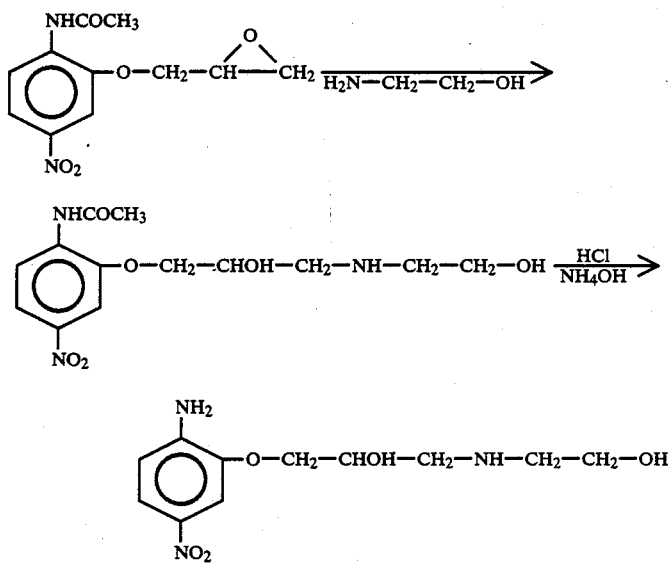

First step

Preparation of 1-(2'-acetylamino-5'-nitrophenoxy)-3-N-(β-hydroxyethyl)-aminopropan-2-ol 10.1 g (0.04 mol) of the 1-(2'-acetylamino-5'-nitrophenoxy)-2,3-epoxypropane prepared according to the first stage of Example 5 are dissolved in 36.6 g of monoethanolamine and 10 ml of absolute alcohol by heating in a boiling water-bath. After heating for 1 hour 30 minutes in the boiling water-bath, the reaction medium is poured into 300 g of iced water. The expected partially deacetylated product precipitates. It is filtered off, washed with water and dried in vacuo. It will be used as such for the second stage of the synthesis.

Second step

Preparation of 1-(2'-amino-5'-nitrophenoxy)-3-N-(β-hydroxyethyl)-aminopropan-2-ol 8.7 g of the crude product obtained in the first stage of the synthesis are heated for 30 minutes, in a boiling water-bath, in 22 ml of hydrochloric acid (specific gravity=1.18). The cooled reaction mixture is treated with ammonia up to a pH of 6. The expected product precipitates in the form of the monohydrochloride. This monohydrochloride is filtered off, recrystallised from an ethanol/water mixture and dried in vacuo. It melts at 156° C.

The monohydrochloride is dissolved in 20 ml of water. The aqueous solution is rendered alkaline with 20% strength ammonia solution. The 1-(2'-amino-5'-nitrophenoxy)-3-N-(β-hydroxyethyl)-aminopropan-2-ol precipitates. The product is filtered off, washed with water, recrystallised from water and dried in vacuo. It melts at 177° C.

The product obtained corresponds to the following analysis results:

| Analysis | Calculated for $C_{11}H_{17}N_3O_5$ | Found |
| --- | --- | --- |
| C % | 48.70 | 48.65 |
| H % | 6.32 | 6.25 |
| N % | 15.49 | 15.44 |
| O % | 29.49 | 29.33 |

EXAMPLE 7

Preparation of 1-(2',5'-diaminophenoxy)-3-aminopropan-2-ol trihydrochloride

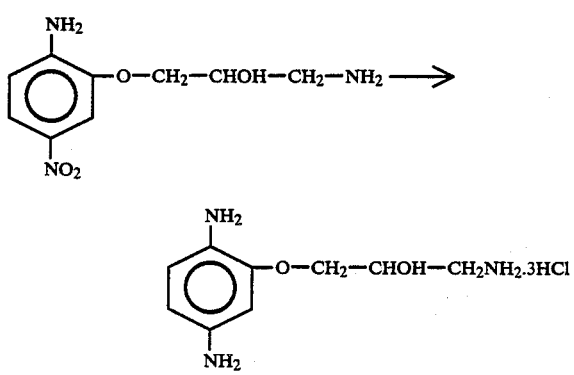

7.5 g of zinc powder and a solution of 0.3 g of ammonium chloride in 1.5 ml of water are added to 15 ml to 96° strength alcohol. The mixture is heated to the reflux temperature, with stirring, and 0.015 mol (3.4 g) of the 1-(2'-amino-5'-nitrophenoxy)-3-aminopropan-2-ol prepared according to Example 5 is then added gradually so as to maintain the reflux without external heating. When the addition has ended, the reflux is maintained for 5 minutes and the boiling reaction medium is then filtered into 4.6 ml of iced hydrochloric acid (specific gravity=1.18). The expected product crystallises in the form of the trihydrochloride. The product is filtered off, washed with alcohol and dried in vacuo. It melts with decomposition at 216°–218° C.

The product obtained corresponds to the following analysis results:

| Analysis | Calculated for $C_9H_{15}N_3O_2.HCl$ | Found |
| --- | --- | --- |
| C % | 35.25 | 34.97 |
| H % | 5.92 | 5.86 |
| N % | 13.70 | 13.82 |
| O % | 10.43 | 10.68 |
| Cl % | 34.69 | 34.52 |

EXAMPLE 8

Preparation of 1-(2',4'-diaminophenoxy)-3-aminopropan-2-ol trihydrochloride

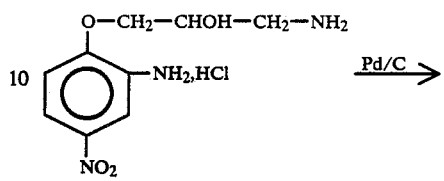

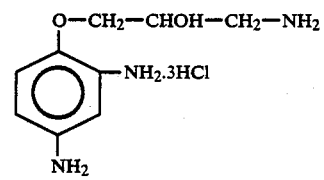

0.02 mol (5.3 g) of the 1-(2'-amino-4'-nitrophenoxy)-3-aminopropan-2-ol monohydrochloride prepared according to Example 4 is introduced into 50 ml of 96° strength alcohol and 0.2 g of 10% strength palladium-on-charcoal. The mixture is heated at 85° C. for one hour under 35 bars of hydrogen. After cooling, it is filtered to remove the catalyst, the filtrate being collected in 20 ml of iced ethanol saturated with hydrogen chloride. The expected product precipitates in the form of the trihydrochloride. After recrystallisation of this trihydrochloride from an ethanol/water mixture, it melts with decomposition at 236°–238° C.

The product obtained corresponds to the following analysis results:

| Analysis | Calculated for $C_9H_{15}N_3O_2.3HCl$ | Found |
| --- | --- | --- |
| C % | 35.23 | 35.41 |
| H % | 5.87 | 5.90 |
| N % | 13.70 | 13.63 |
| O % | 10.44 | 10.63 |
| Cl % | 34.75 | 34.85 |

It has been found, surprisingly, that this compound, which constitutes a coupler, gives, on coupling with paraaminophenol, much redder tints than its homologue which does not contain an OH group on the side chain; it has also been found, surprisingly, that the red tints obtained are much more stable than in the case of the non-hydroxylated homologue.

EXAMPLE 9

Preparation of 1-(3'-methylamino-4'-nitrophenoxy)-3-aminopropan-2-ol hydrochloride

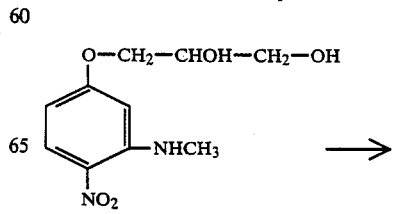

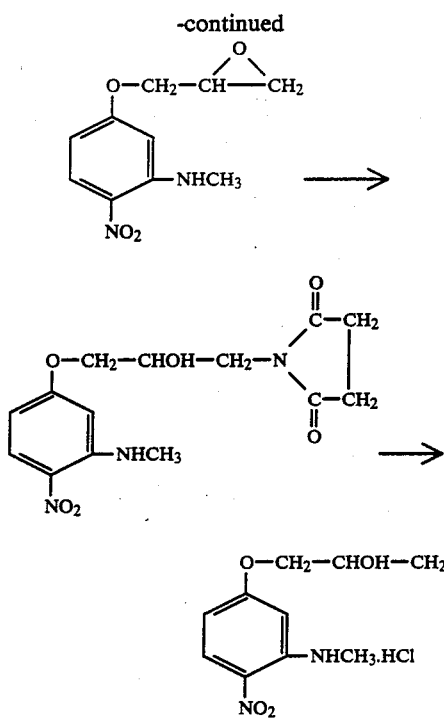

First step

Preparation of 1-(3'-methylamino-4'-nitrophenoxy)-2,3-epoxypropane 0.15 mol (36.3 g) of 3-N-methylamino-4-nitrophenyl β,γ-dihydroxypropyl ether (product described in Example 2 of French patent application No. 80/17,617) is dissolved in 150 ml of pyridine at ambient temperature. 0.22 mol (25.2 g) of methanesulphonyl chloride is added dropwise, in the course of 10 minutes and with stirring, to this pyridine solution kept at −5° C. When the addition has ended, the temperature of the reaction medium is allowed to rise to about 20° C., and then, after the reaction medium has been left to stand for 45 minutes at ambient temperature, 100 ml of 27.8% strength methanolic solution of sodium methylate are added thereto, at −5° C., in the course of 10 minutes. When the addition has ended, the mixture is stirred for 2 hours at ambient temperature and the methylene chloride is then washed with water, with 1 N hydrochloric acid solution and then with a saturated solution of sodium bicarbonate. The methylene chloride is driven off in vacuo. The expected product, consisting of the residual oil, crystallises very rapidly. After recrystallisation from ethyl acetate and drying in vacuo, it melts at 113° C.

The product obtained corresponds to the following analysis results:

| Analysis | Calculated for $C_{10}H_{12}N_2O_4$ | Found |
|---|---|---|
| C % | 53.57 | 53.66 |
| H % | 5.39 | 5.35 |
| N % | 12.50 | 12.48 |
| O % | 28.54 | 28.58 |

Second step

Preparation of 1-(3'-methylamino-4'-nitrophenoxy)-3-succinimidopropan-2-ol 0.087 mol (19.5 g) of 1-(3'-methylamino-4'-nitrophenoxy)-2,3-epoxypropane is dissolved in 75 ml of absolute alcohol to which 6 drops of pyridine have been added. 0.10 mol (10.1 g) of succinimide is added and the mixture is then heated under reflux for 4 hours. The reaction mixture is filtered at the boil. On cooling of the filtrate, the expected product crystallises. After recrystallisation from alcohol and drying in vacuo, it melts at 152° C.

The product obtained corresponds to the following analysis results:

| Analysis | Calculated for $C_{14}H_{17}N_3O_6$ | Found |
|---|---|---|
| C % | 52.01 | 51.97 |
| H % | 5.30 | 5.36 |
| N % | 13.00 | 12.98 |
| O % | 29.69 | 29.50 |

Third step

Preparation of 1-(3'-methylamino-4'-nitrophenoxy)-3-aminopropan-2-ol monohydrochloride 10.5 g (0.0324 mol) of the succinimido derivative obtained according to the second step are heated under reflux for 7 hours in 20 ml of 96° strength alcohol and 60 ml of 36% strength hydrochloric acid. The reaction medium is cooled to 0° C. The expected product crystallises. It is filtered off, washed with acetone and recrystallised from a mixture of water and alcohol. After drying in vacuo, it melts with decomposition at between 258° and 260°C.

The product obtained corresponds to the following analysis results:

| Analysis | Calculated for $C_{10}H_{15}N_3O_4 \cdot HCl$ | Found |
|---|---|---|
| C % | 43.25 | 43.21 |
| H % | 5.81 | 5.78 |
| N % | 15.13 | 15.11 |
| O % | 23.04 | 23.10 |
| Cl % | 12.77 | 12.70 |

EXAMPLE 10

Preparation of 1-(2',4'-diaminophenoxy)-3-dimethylaminopropan-2-ol trihydrochloride monohydrate

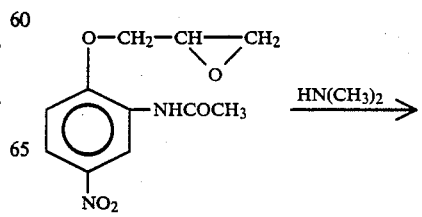

-continued

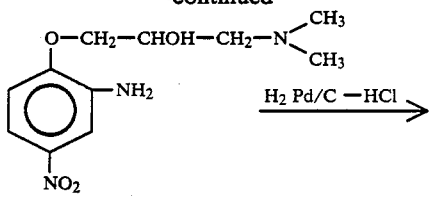

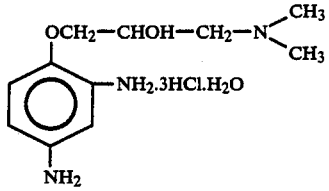

First step
Preparation of 1-(2'-amino-4'-nitrophenoxy)-3-dimethylaminopropan-2-ol 0.085 mol (21.5 g) of 1-(2'-acetylamino-4'-nitrophenoxy)-2,3-epoxypropane (compound described in Example (4) is introduced into 100 ml of a 40% strength aqueous solution of dimethylamine, and the reaction mixture is stirred for 30 minutes at ambient temperature. After dilution by the addition of 225 ml of iced water, followed by neutralisation with acetic acid, the mixture is evaporated to dryness in vacuo. The dried residue is taken up in 150 ml of ethyl acetate. After washing with acetone, the material which is insoluble in ethyl acetate consists of 28.5 g of 1-(2'-acetylamino-4'-nitrophenoxy)-3-dimethylaminopropan-2-ol. This acetylated derivative is heated under reflux for two hours in 220 ml of ethanol saturated with hydrogen chloride. After the reaction medium has cooled, the expected product in the form of the hydrochloride is filtered off. After this hydrochloride has been dissolved in water and the aqueous solution has been rendered alkaline with sodium hydroxide solution, the 1-(2'-amino-4'-nitrophenoxy)-3-dimethylaminopropan-2-ol is precipitated in the form of crystals.

The product is filtered off, washed with water and dried in vacuo. It melts at 123° C.

Elementary analysis gives the following results:

| Analysis | Calculated for $C_{11}H_{17}N_3O_4$ | Found |
|---|---|---|
| C % | 51.76 | 51.65 |
| H % | 6.67 | 6.72 |
| N % | 16.47 | 16.40 |
| O % | 25.10 | 25.02 |

Second step
Preparation of 1-(2',4'-diaminophenoxy)-3-dimethylaminopropan-2-ol trihydrochloride monohydrate A solution of 0.12 mol (30.6 g) of 1-(2'-amino-4'-nitrophenoxy)-3-dimethylaminopropan-2-ol in 92 ml of absolute alcohol is subjected to catalytic hydrogenation at 80° C., under a pressure of 40 bars of hydrogen, in the presence of 4.5 g of 10% strength palladium-on-charcoal. The catalyst is removed by filtration, the alcoholic filtrate being received in 143 ml of iced ethanol saturated with hydrogen chloride. The expected product precipitates in the form of the trihydrochloride. This trihydrochloride is filtered off and recrystallised from an aqueous-alcoholic solution of hydrochloric acid. After drying in vacuo, it melts with decomposition at between 205° and 206° C.

Elementary analysis gives the following results:

| Analysis | Calculated for $C_{11}H_{19}N_3O_2.3HCl.H_2O$ | Found |
|---|---|---|
| C % | 37.44 | 37.31 |
| H % | 6.81 | 6.87 |
| N % | 11.91 | 11.79 |
| O % | 13.62 | 13.89 |
| Cl % | 30.21 | 30.07 |

EXAMPLE 11
Preparation of 2-hydroxy-3-(2',4'-diaminophenoxy)-propyltrimethylammonium chloride dihydrochloride hemihydrate

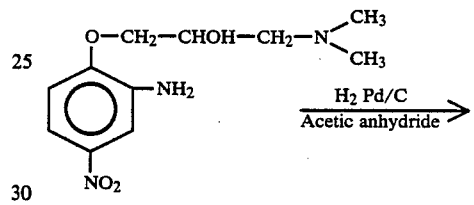

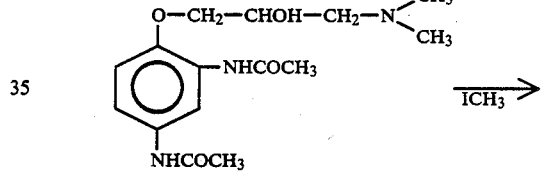

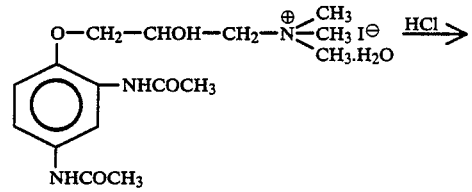

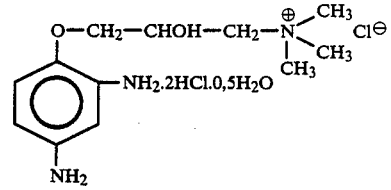

First step
Preparation of 1-(2',4'-diacetylaminophenoxy)-3-dimethylaminopropan-2-ol Under the conditions described in the second step of Example 10, an alcoholic solution of 0.1 mol (25.5 g) of 1-(2'-amino-4'-nitrophenoxy)-3-dimethylaminopropan-2-ol is subjected to catalytic hydrogenation in the presence of palladium-on-charcoal. The catalyst is removed by filtration, the solvent is driven off in vacuo, the oily residue is taken up in 200 ml of ethyl acetate, and 17 ml of acetic anhydride are added gradually thereto. The expected diacetylated derivative precipitates in the form of crystals. It is filtered off, washed with acetone and dried in vacuo. It melts at 118°–120° C.

Second step

Preparation of
2-hydroxy-3-(2′,4′-diacetylaminophenoxy)-propyl-trimethylammonium iodide monohydrate 0.03 mol (9.3 g) of the diacetylated derivative obtained in the first step is dissolved in 30 ml of acetone to which 3 ml of water has been added. The solution is heated to 50° C. and 0.06 mol (3.75 ml) of methyl iodide is then added thereto, with stirring. The reaction medium is kept at 50° C. for 30 minutes. The expected quaternary derivative precipitates. It is filtered off, washed with acetone and dried. It melts with decomposition at between 159° and 160° C.

Elementary analysis gives the following results:

| Analysis | Calculated for $C_{16}H_{26}O_4N_3I.H_2O$ | Found |
| --- | --- | --- |
| C % | 40.94 | 40.87 |
| H % | 5.97 | 6.02 |
| N % | 8.95 | 8.87 |
| O % | 17.06 | 17.21 |
| I % | 27.08 | 27.02 |

Third step

Preparation of
2-hydroxy-3-(2′,4′-diaminophenoxy)-propyltrimethylammonium dihydrochloride hemihydrate 0.0137 mol (6.2 g) of the quaternary salt obtained in the second step is heated under reflux for 3 hours in 30 ml of ethanol saturated with hydrogen chloride. The expected product precipitates. It is filtered off, washed with absolute alcohol and dried in vacuo. It melts with decomposition at between 258° and 260° C.

Elementary analysis gives the following results:

| Analysis | Calculated for $C_{12}H_{22}N_3O_2Cl.2HCl.\frac{1}{2}H_2O$ | Found |
| --- | --- | --- |
| C % | 40.28 | 40.51 |
| H % | 6.99 | 6.72 |
| N % | 11.75 | 11.77 |
| O % | 11.19 | 11.21 |
|  | 29.80 | 29.95 |

EXAMPLE 12

The following dyeing composition is prepared:

| 1-(3′-Nitro-4′-aminophenoxy)-3-aminopropan-2-ol | 0.2 g |
| --- | --- |
| 2-Butoxyethanol | 10 g |
| Hydroxyethylcellulose | 2 g |
| Ammonium lauryl-sulphate | 5 g |
| Water qs | 100 g |

The pH of the composition is equal to 8.4.

When applied to bleached hair for 20 minutes at 30° C., this mixture imparts to the hair, after rinsing and shampooing, a colouration of 7 YR 7/14 (determined on the "Munsell" scale).

EXAMPLE 13

The following dyeing composition is prepared:

| 1-(2′-Amino-4′-nitrophenoxy)-3-aminopropan-2-ol | 0.8 g |
| --- | --- |
| 2-Butoxyethanol | 10 g |
| Acrylic acid polymer having a molecular weight of 2 to 3 million, sold under the name "CARBOPOL 934" by "GOODRICH CHEMICAL CO" | 2 g |
| Ammonia solution (22° Be strength) | 2 g |
| Water qs | 100 g |

The pH of the composition is equal to 6.7.

When applied to bleached hair for 35 minutes at 30° C., this mixture imparts to the hair, after rinsing and shampooing, a colouration of 3.75 Y 8.5/9.5 (determined on the "Munsell" scale).

EXAMPLE 14

The following dyeing composition is prepared:

| 1-(3′-Nitro-4′-aminophenoxy)-3-N,N—diethylamino-propan-2-ol hydrochloride | 0.6 g |
| --- | --- |
| Propylene glycol | 10 g |
| Diethanolamides of copra fatty acids | 2.2 g |
| Lauric acid | 0.8 g |
| Ethylene glycol monoethyl ether | 2 g |
| Monoethanolamine | 1 g |
| Water qs | 100 g |

The pH of the composition is equal to 7.8.

When applied to bleached hair for 25 minutes at 30° C., this mixture imparts to the hair, after rinsing and shampooing, a colouration of 7.5 YR 7/16 (determined on the "Munsell" scale).

EXAMPLE 15

The following dyeing composition is prepared:

| 1-(2′-Amino-5′-nitrophenoxy)-3-aminopropan-2-ol | 0.55 g |
| --- | --- |
| Propylene glycol | 10 g |
| Lauric acid monoethanolamide | 1.5 g |
| Lauric acid | 1 g |
| Hydroxyethylcellulose | 5 g |
| Monoethanolamine | 2 g |
| Water qs | 100 g |

The pH of the composition is equal to 10.

When applied to bleached hair for 25 minutes at 25° C., this mixture imparts to the hair, after rinsing and shampooing, a colouration of 6.25 Y 8.5/12 (determined on the "Munsell" scale).

EXAMPLE 16

The following dyeing composition is prepared:

| 1-(3′-Nitro-4′-aminophenoxy-3-N—propylaminopropan-2-ol monohydrochloride | 1 g |
| --- | --- |
| 2-Butoxyethanol | 10 g |
| Cetyl/stearyl alcohol sold under the name "ALFOL C16/18" by "CONDEA" | 8 g |
| Sodium cetyl/stearyl-sulphate sold under the name "LANETTE WAX E" by "HENKEL" | 0.5 g |
| Oxyethyleneated castor oil sold under the name "CEMULSOL B" by "RHONE-POULENC" | 1 g |
| Oleic diethanolamide | 1.5 g |
| Ammonia solution (22° C. Be strength) | 0.25 g |
| Water qs | 100 g |

The pH of the composition is equal to 8.7.

When applied to bleached hair for 35 minutes at 28° C., this mixture imparts to the hair, after rinsing and shampooing, a colouration of 7 YR 7/16 (determined on the "Munsell" scale).

EXAMPLE 17

The following dyeing composition is prepared:

| | |
|---|---|
| 1-(2'-Amino-5'-nitrophenoxy)-3-N—(β-hydroxyethyl)-aminopropan-2-ol | 0.4 g |
| 2-Butoxyethanol | 10 g |
| Cetyl/stearyl alcohol sold under the name "ALFOL C16/18" by "CONDEA" | 8 g |
| Sodium cetyl/stearyl-sulphate sold under the name "LANETTE WAX E" by "HENKEL" | 0.5 g |
| Oxyethyleneated castor oil sold under the name "CEMULSOL B" by "RHONE-POULENC" | 1 g |
| Oleic diethanolamide | 1.5 g |
| Triethanolamine (containing 10% of active ingredient) | 0.4 g |
| Water qs | 100 g |

The pH of the composition is equal to 8.7.

When applied to bleached hair for 30 minutes at 28° C., this mixture imparts to the hair, after rinsing and shampooing, a colouration of 7.5 Y 8.5/11 (determined on the "Munsell" scale).

EXAMPLE 18

The following dyeing composition is prepared:

| | |
|---|---|
| 1-(3'-Nitro-4'-aminophenoxy)-3-N—propylamino-propan-2-ol hydrochloride | 0.15 g |
| 3-Nitro-4-N'—methylamino-N—(β-aminoethyl)-aniline dihydrochloride | 0.076 g |
| 2-Butoxyethanol | 10 g |
| Hydroxyethylcellulose sold under the name "CELLOSIZE WP03" by "UNION CARBIDE" | 2 g |
| Dimethyl-alkyl-hydroxyethyl-ammonium bromide (alkyl = tallow derivative) | 2 g |
| Ammonia solution (22° Be strength) | 0.25 g |
| Water qs | 100 g |

The pH of the composition is equal to 8.5.

When applied to 90% naturally white hair for 25 minutes at 28° C., this mixture imparts to the hair, after rinsing and shampooing, a coppery light chestnut colouration.

EXAMPLE 19

The following dyeing composition is prepared:

| | |
|---|---|
| 1-(3'-Nitro-4'-aminophenoxy)-3-N,N—diethylamino-propan-2-ol hydrochloride | 0.05 g |
| 3-Nitro-4-N'—(β-aminoethyl)-amino-N,N—di-(β-hydroxyethyl)-aniline dihydrochloride | 0.07 g |
| 3-Nitro-4-amino-6-methyl-N—(β-hydroxyethyl)-aniline | 0.03 g |
| 2-Butoxyethanol | 10 g |
| Nonylphenol oxyethyleneated with 4 mols of ethylene oxide, sold under the name "CEMULSOL NP4" by "RHONE-POULENC" | 12 g |
| Nonylphenol oxyethyleneated with 9 mols of ethylene oxide, sold under the name "CEMULSOL NP9" by "RHONE-POULENC" | 15 g |
| Oleyl alcohol oxyethyleneated with two mols of ethylene oxide | 1.5 g |
| Oleyl alcohol oxyethyleneated with four mols of ethylene oxide | 1.5 g |
| Triethanolamine (containing 20% of active ingredient) | 1.5 g |
| Water qs | 100 g |

The pH of the composition is equal to 8.4.

When applied to 90% naturally white hair for 20 minutes at 28° C., this mixture imparts to the hair, after rinsing and shampooing, a pinkish beige colouration.

EXAMPLE 20

The following dyeing composition is prepared:

| | |
|---|---|
| 1-(2'-Amino-4'-nitrophenoxy)-3-aminopropan-2-ol | 0.2 g |
| 3-Nitro-4-N—(β-hydroxyethyl)-aminophenyl β-hydroxypropyl ether | 0.08 g |
| 3-Nitro-4-amino-N—(β-hydroxypropyl)-aniline | 0.06 g |
| 2-[4'-(N,N—dihydroxyethylamino)-anilino]-5-N'—(β-hydroxyethyl)-amino-1,4-benzoquinone | 0.5 g |
| 2-Butoxyethanol | 10 g |
| Diethanolamides of copra fatty acids | 2.2 g |
| Lauric acid | 0.8 g |
| Ethylene glycol monoethyl ether | 2 g |
| Monoethanolamine | 1 g |
| Water qs | 100 g |

The pH of the composition is equal to 7.

When applied to bleached hair for 20 minutes at 30° C., this mixture imparts to the hair, after rinsing and shampooing, a coppery blond colouration.

EXAMPLE 21

The following dyeing composition is prepared:

| | |
|---|---|
| 1-(3'-Nitro-4'-aminophenoxy)-3-N—propylaminopropan-2-ol monohydrochloride | 0.065 g |
| 2-N—(β-Hydroxyethyl)-amino-5-nitrophenol | 0.035 g |
| 3-Nitro-4-N'—methylamino-N,N—di-(β-hydroxyethyl)-aniline | 0.21 g |
| 3-Nitro-4-amino-6-methyl-N—(β,γ-dihydroxypropyl)-aniline | 0.05 g |
| 2-Butoxyethanol | 10 g |
| Carboxymethylcellulose | 2 g |
| Ammonium lauryl-sulphate | 5 g |
| Triethanolamine (containing 20% of active ingredient) | 0.125 g |
| Water qs | 100 g |

The pH of the composition is equal to 7.

When applied to bleached hair for 25 minutes at 30° C., this mixture imparts to the hair, after rinsing and shampooing, a golden sandy colouration.

EXAMPLE 22

The following dyeing composition is prepared:

| | |
|---|---|
| 1-(3'Nitro-4'-aminophenoxy)-3-aminopropan-2-ol | 0.055 g |
| 1,4,5,8-Tetraaminoanthraquinone | 0.105 g |
| 2-Amino-3-nitrotoluene | 0.035 g |
| 3-Nitro-4-amino-6-methyl-N—(β-aminoethyl)-aniline | 0.03 g |
| Propylene glycol | 10 g |
| Cetyl/stearyl alcohol sold under the name "ALFOL C16/18" by "CONDEA" | 8 g |
| Sodium cetyl/stearyl-sulphate sold under the name "LANETTE WAX E" by "HENKEL" | 0.5 g |
| Oxyethyleneated castor oil sold under the name "CEMULSOL B" by "RHONE-POULENC" | 1 g |
| Oleic diethanolamide | 1.5 g |
| Triethanolamine (containing 20% of active ingredient) | 2 g |
| Water qs | 100 g |

The pH of the composition is equal to 9.

When applied to 90% naturally white hair for 40 minutes at 28° C., this mixture imparts to the hair, after rinsing and shampooing, a golden blond colouration.

EXAMPLE 23

The following dyeing composition is prepared:

| | |
|---|---|
| 1-(2'-Amino-5'-nitrophenoxy)-3-aminopropan-2-ol | 0.1 g |
| 3-Nitro-4-N—(β-aminoethyl)-aminophenoxyethanol | 0.15 g |
| 3-Nitro-4-amino-6-methyl-N—(β,γ-dihydroxypropyl)-aniline | 0.05 g |
| 3-Nitro-4-N'—methylamino-N,N—di-(β-hydroxyethyl)-aniline | 0.5 g |
| Propylene glycol | 10 g |
| Hydroxyethylcellulose sold under the name "CELLOSIZE WP03" by "UNION CABIDE" | 2 g |
| Dimethyl-alkyl-hydroxyethyl-ammonium bromide (alkyl = tallow derivative) | 2 g |
| Ammonia solution qs | pH 8 |
| Water qs | 100 g |

When applied for 25 minutes at 28° C. to hair which has been bleached straw yellow, this mixture imparts to the hair, after rinsing and shampooing, a very coppery chestnut colouration.

EXAMPLE 24

The following dyeing composition is prepared:

| | |
|---|---|
| 1-(3'-Nitro-4'-aminophenoxy)-3-aminopropan-2-ol | 0.5 g |
| 1-(2'-Amino-5'-nitrophenoxy)-3-aminopropan-2-ol | 0.2 g |
| 3-Nitro-4-amino-N—(β-hydroxyethyl)-aniline | 0.15 g |
| 3-Nitro-2-N'—(β-aminoethyl)-amino-N,N—di-(β-hydroxyethyl)-aniline dihydrochloride | 0.2 g |
| Hydroxyethylcellulose | 2 g |
| Ammonium lauryl-sulphate | 5 g |
| Ammonia solution (22° Be strength) | 0.25 g |
| Water qs | 100 g |

The pH of the composition is equal to 9.

When applied to bleached hair for 20 minutes at 28° C., this mixture imparts to the hair, after rinsing and shampooing, a reddish copper colouration.

EXAMPLE 25

The following dyeing composition is prepared:

| | |
|---|---|
| 1-(2',4'-Diaminophenoxy)-3-aminopropan-2-ol trihydrochloride | 0.11 g |
| Resorcinol | 0.08 g |
| Para-phenylenediamine | 0.3 g |
| 4-Amino-N,N—di-(β-hydroxyethyl)-aniline dihydrochloride | 0.6 g |
| 3-Nitro-4-amino-N—(β-hydroxypropyl)-aniline | 0.5 g |
| 3-N—Methylamino-4-nitrophenoxyethanol | 0.3 g |
| Cetyl/stearyl alcohol sold under the name "ALFOL C16/18" by "CONDEA" | 8 g |
| Sodium cetyl/stearyl-sulphate sold under the name "LANETTE WAX E" by "HENKEL" | 0.5 g |
| Oxyethyleneated castor oil sold under the name "CEMULSOL B" by "RHONE-POULENC" | 1 g |
| Oleic diethanolamide | 1.5 g |
| Pentasodium salt of diethylenetriaminepentaacetic acid, sold under the name "MASQUOL DTPA" | 2.5 g |
| Sodium bisulphite solution (35° Be strength) | 1 g |
| Ammonia solution (22° Be strength) | 11 g |
| Water qs | 100 g |

The pH of the composition is equal to 10.1.

100 g of hydrogen peroxide of 20 volumes strength are added at the time of use.

When applied for 30 minutes at 30° C. to hair which has been bleached straw yellow, this mixture imparts to the hair, after rinsing and shampooing, a black-brown colouration.

EXAMPLE 26

The following dyeing composition is prepared:

| | |
|---|---|
| 1-(2',4'-Diaminophenoxy)-3-aminopropan-2-ol trihydrochloride | 0.4 g |
| Resorcinol | 0.1 g |
| Meta-aminophenol | 0.13 g |
| Para-phenylenediamine | 0.125 g |
| Para-aminophenol | 0.13 g |
| N—Methyl-para-aminophenol sulphate | 0.3 g |
| 2-Methyl-4-amino-5-nitrophenol | 0.4 g |
| Nonylphenol oxyethyleneated with 4 mols of ethylene oxide, sold under the name "REMCOPAL 334" by "GERLAND" | 21 g |
| Nonylphenol oxyethyleneated with 9 mols of ethylene oxide, sold under the name "REMCOPAL 349" by "GERLAND" | 24 g |
| Oleic acid | 4 g |
| 2-Butoxyethanol | 3 g |
| Ethanol (96° Be strength) | 10 g |
| Pentasodium salt of diethylenetriaminepentaacetic acid, sold under the name "MASQUOL DTPA" | 2.5 g |
| Sodium bisulphite solution (35° Be strength) | 1 g |
| Ammonia solution (22° strength) | 10 g |
| Water qs | 100 g |

The pH of the composition is equal to 10.5.

75 g of hydrogen peroxide of 20 volumes strength are added at the time of use.

When applied to 90% naturally white hair for 25 minutes at 30° C., this mixture imparts to the hair, after rinsing and shampooing, an ashen chestnut colouration.

EXAMPLE 27

The following dyeing composition is prepared:

| | |
|---|---|
| 1-(2',5'-Diaminophenoxy)-3-aminopropan-2-ol trihydrochloride | 0.153 g |
| 2,6-Dimethyl-3-acetylaminophenol | 0.089 g |
| Nonylphenol oxyethyleneated with 4 mols of ethylene oxide, sold under the name "REMCOPAL 334" by "GERLAND" | 21 g |
| Nonylphenol oxyethyleneated with 9 mols of ethylene oxide, sold under the name "REMCOPAL 349" by "GERLAND" | 24 g |
| Oleic acid | 4 g |
| 2-Butoxyethanol | 3 g |
| Ethanol (96° strength) | 10 g |
| Pentasodium salt of diethylenetriaminepentaacetic acid, sold under the name "MASQUOL DTPA" | 3.5 g |
| Ammonia solution (22° Be strength) | 10 g |
| Water qs | 100 g |

The pH of the composition is equal to 10.5.

100 g of hydrogen peroxide of 20 volumes strength are added at the time of use.

When applied to 90% naturally white hair for 25 minutes at 30° C., this mixture imparts to the hair, after rinsing and shampooing, a bluish grey colouration.

EXAMPLE 28

The following dyeing composition is prepared:

| | |
|---|---|
| 1-(2',5'-Diaminophenoxy)-3-aminopropan-2-ol trihydrochloride | 0.63 g |
| 2-Methylresorcinol | 0.14 g |
| 3-Acetylaminophenol | 0.135 g |
| 2,4-Diaminophenoxyethanol dihydrochloride | 0.06 g |
| 3-Nitro-4-amino-6-methyl-N—(β-hydroxyethyl)-aniline | 0.215 g |
| 1-(3'-Nitro-4'-aminophenoxy)-3-aminopropan-2-ol | 0.3 g |
| Acrylic acid polymer having a molecular weight of 2 to 3 million, sold under the name "CARBAPOL | 1.5 g |

-continued

| | |
|---|---|
| 934" by "GOODRICH CHEMICAL CO" | |
| Alcohol (96° strength) | 11 g |
| 2-Butoxyethanol | 5 g |
| Trimethylcetylammonium bromide | 1 g |
| Ethylenediaminetetraacetic acid sold under the name "TRILON B" | 0.1 g |
| Ammonia solution (22° Be strength) | 10 g |
| Thioglycolic acid | 0.2 g |
| Water qs | 100 g |

The pH of the composition is equal to 10.

100 g of hydrogen peroxide of 20 volumes strength are added at the time of use.

When applied for 25 minutes at 30° C. to hair which has been bleached straw yellow, this mixture imparts to the hair, after rinsing and shampooing, a chestnut colouration.

EXAMPLE 29

The following dyeing composition is prepared:

| | |
|---|---|
| 1-(2',5'-Diaminophenoxy)-3-aminopropan-2-ol trihydrochloride | 0.306 g |
| 2,4-Diaminophenyl β-hydroxypropyl ether dihydrochloride | 0.255 g |
| Nonylphenol oxyethyleneated with 4 mols of ethylene oxide, sold under the name "CEMULSOL NP$_4$" by "RHONE-POULENC" | 12 g |
| Nonylphenol oxyethyleneated with 9 mols of ethylene oxide, sold under the name "CEMULSOL NP$_9$" by "RHONE-POULENC" | 15 g |
| Oleyl alcohol oxyethyleneated with two mols of ethylene oxide | 1.5 g |
| Oleyl alcohol oxyethyleneated with four mols of ethylene oxide | 1.5 g |
| Propylene glycol | 6 g |
| Ethylenediaminetetraacetic acid sold under the name "TRILON B" | 0.12 g |
| Ammonia solution (22° Be strength) | 11 g |
| Thioglycolic acid | 0.6 g |
| Water qs | 100 g |

The pH of the composition is equal to 9.9.

100 g of hydrogen peroxide of 20 volumes strength are added at the time of use.

When applied to 90% naturally white hair for 30 minutes at 28° C., this mixture imparts to the hair, after rinsing and shampooing, a pure blue colouration.

EXAMPLE 30

The following dyeing composition is prepared:

| | |
|---|---|
| 1-(2',4'-Diaminophenoxy)-3-aminopropan-2-ol trihydrochloride | 0.25 g |
| Para-phenylenediamine | 0.088 g |
| Oleyl alcohol oxyethyleneated with two mols of ethylene oxide | 4.5 g |
| Oleyl alcohol oxyethyleneated with four mols of ethylene oxide | 4.5 g |
| Oleylamine oxyethyleneated with 12 mols of ethylene oxide, sold under the name "ETHOMEEN TO$_{12}$" by "ARMOUR HESS" | 4.5 g |
| Diethanolamides of copra fatty acids | 9 g |
| Propylene glycol | 4 g |
| 2-Butoxyethanol | 8 g |
| Ethanol (96° strength) | 6 g |
| Pentasodium salt of diethylenetriaminepentaacetic acid, sold under the name "MASQUOL DTPA" | 2 g |
| Thioglycolic acid | 0.5 g |
| Ammonia solution (22° Be strength) | 10 g |
| Water qs | 100 g |

The pH of the composition is equal to 10.3.

85 g of hydrogen peroxide of 20 volumes strength are added at the time of use.

When applied to 90% naturally white hair for 25 minutes at 30° C., this mixture imparts to the hair, after rinsing and shampooing, a midnight blue colouration.

EXAMPLE 31

The following dyeing composition is prepared:

| | |
|---|---|
| 1-(2',4'-Diaminophenoxy)-3-aminopropan-2-ol trihydrochloride | 0.12 g |
| Para-aminophenol | 0.043 g |
| Cetyl/stearyl alcohol sold under the name "ALFOL C16/18" by "CONDEA" | 19 g |
| 2-Octyldodecanol sold under the name "EUTANOL G" by "HENKEL" | 4.5 g |
| Cetyl/steary alcohol containing 15 mols of ethylene oxide, sold under the name "MERGITAL CS 15/E" by "HENKEL" | 2.5 g |
| Ammonium lauryl-sulphate containing 30% of active ingredient | 12 g |

Cationic polymer possessing repeat units:

$$\left[ {}^{\oplus}N{\overset{CH_3}{\underset{CH_3}{\diagdown}}}(CH_2)_3 - N{\overset{CH_3}{\underset{CH_3}{\diagup}}}{}^{\oplus}-(CH_2)_6 \right] \quad\quad 4\,g$$
$$Cl^{\ominus} \quad\quad Cl^{\ominus}$$

| | |
|---|---|
| Benzyl alcohol | 2 g |
| Ammonia solution (22° Be strength) | 11 g |
| Ethylenediaminetetraacetic acid sold under the name "TRILON B" | 1 g |
| Sodium sulphite | 1.2 g |
| Water qs | 100 g |

The pH of the composition is equal to 10.

75 g of hydrogen peroxide of 20 volumes strength are added at the time of use.

When applied to bleached hair for 20 minutes at 28° C., this mixture imparts to the hair, after rinsing and shampooing, a pink champagne colouration.

EXAMPLE 32

The following dyeing composition is prepared:

| | |
|---|---|
| 1-(2',4'-Diaminophenoxy)-3-aminopropan-2-ol trihydrochloride | 0.05 g |
| Resorcinol | 0.15 g |
| Meta-aminophenol | 0.085 g |
| 2-Methyl-5-N—(β-hydroxyethyl)-aminophenol | 0.09 g |
| Para-phenylenediamine | 0.1 g |
| 2-Amino-3-nitrophenol | 0.405 g |
| 3-Nitro-4-amino-6-methyl-N—(β-aminoethyl)-aniline | 0.08 g |
| Acrylic acid polymer having a molecular weight of 2 to 3 million, sold under the name "CARBOPOL 934" by "GOODRICH CHEMICAL CO" | 1.5 g |
| Alcohol (96° strength) | 11 g |
| 2-Butoxyethanol | 5 g |
| Trimethylcetylammonium bromide | 1 g |
| Ethylenediaminetetraacetic acid sold under the name "TRILON B" | 0.1 g |
| Ammonia solution (22° Be strength) | 10 g |
| Thioglycolic acid | 0.2 g |
| Water qs | 100 g |

The pH of the composition is equal to 10.3.

100 g of hydrogen peroxide of 20 volumes strength are added at the time of use.

When applied for 30 minutes at 28° C. to hair which has been bleached straw yellow, this mixture imparts to the hair, after rinsing and shampooing, a reddish copper medium chestnut colouration.

EXAMPLE 33

The following dyeing composition is prepared:

| | |
|---|---|
| 1-(3'-methylamino-4'-nitrophenoxy)-2-amino-propanol monohydrochloride | 0.3 g |
| 3-Nitro-4-amino-6-methyl-N—(β-hydroxyethyl)-aniline | 0.8 g |
| 1,4,5,8-Tetraaminoanthraquinone | 0.06 g |
| 2-Butoxyethanol | 10 g |
| Hydroxyethylcellulose sold under the name "CELLOSIZE WP03" by "UNION CARBIDE" | 2 g |
| Dimethyl-alkyl-hydroxyethyl-ammonium bromide (alkyl = tallow derivative) | 2 g |
| Ammonium solution (5% strength) | 1 g |
| Water qs | 100 g |

The pH of the composition is equal to 7.

When applied to bleached hair for 20 minutes at 30° C., this mixture imparts to the hair, after rinsing and shampooing, a light copper colouration.

EXAMPLE 34

The following dyeing composition is prepared:

| | |
|---|---|
| 1-(3'-Methylamino-4'-nitrophenoxy)-2-amino-propanol monohydrochloride | 1 g |
| 2-Butoxyethanol | 10 g |
| Cetyl/stearyl alcohol sold under the name "ALFOL C16/18" by "CONDEA" | 8 g |
| Sodium cetyl/stearyl-sulphate sold under the name "LANETTE WAX E" by "HENKEL" | 0.5 g |
| Oxyethyleneated castor oil sold under the name "CEMULSOL B" by "RHONE-POULENC" | 1 g |
| Oleic diethanolamide | 1.5 g |
| Triethanolamine (in 20% strength aqueous solution) | 2 g |
| Water qs | 100 g |

The pH of the composition is equal to 7.5.

When applied to bleached hair for 30 minutes at 28° C., this mixture imparts to the hair, after rinsing and shampooing, a colouration of 4.5 Y 8.5/13 (determined on the "Munsell" scale).

EXAMPLE 35

The following dyeing composition is prepared:

| | |
|---|---|
| 1-(2',4'-Diaminophenoxy)-3-dimethylaminopropan-2-ol trihydrochloride monohydrate | 0.836 g |
| Para-phenylenediamine | 0.256 g |
| Nonylphenol containing 4 mols of ethylene oxide, sold by "RHONE POULENC" under the name "CEMULSOL NP4" | 21 g |
| Nonylphenol containing 9 mols of ethylene oxide, sold by "RHONE POULENC" under the name "CEMUSOL NP9" | 24 g |
| Oleic acid | 4 g |
| 2-Butoxyethanol | 3 g |
| Ethanol (96° strength) | 10 g |
| Pentasodium salt of diethylenetriaminepentaacetic acid, sold under the name "MASQUOL DTPA" | 2.5 g |
| Thioglycolic acid | 0.6 g |
| Ammonia solution (22° Be strength) | 10 g |
| Water qs | 100 g |

The pH of the composition is equal to 10.2.

120 g of hydrogen peroxide of 20 volumes strength are added at the time of use.

When applied to 90% naturally white hair for 25 minutes at 28° C., this mixture imparts to the hair, after rinsing and shampooing, a midnight blue colouration.

EXAMPLE 36

The following dyeing composition is prepared:

| | |
|---|---|
| 2-Hydroxy-3-(2',4'-diaminophenoxy)-propyl-trimethylammonium chloride dihydrochloride hemihydrate | 0.35 g |
| Para-phenylenediamine | 0.108 g |
| Nonylphenol oxyethyleneated with 4 mols of ethylene oxide, sold under the name "REMCOPAL 334" by "GERLAND" | 21 g |
| Nonylphenol oxyethyleneated with 9 mols of ethylene oxide, sold under the name "REMCOPAL 349" by "GERLAND" | 24 g |
| Oleic acid | 4 g |
| 2-Butoxyethanol | 3 g |
| Ethanol (96° strength) | 10 g |
| Pentasodium salt of diethylenetriaminepentaacetic acid, sold under the name "MASQUOL DTPA" | 2.5 g |
| Sodium bisulphite solution (35° Be strength) | 1 g |
| Ammonia solution (22° Be strength) | 10 g |
| Water qs | 100 g |

The pH of the composition is equal to 10.

100 g of hydrogen peroxide of 20 volumes strength are added at the time of use.

When applied to 90% naturally white hair for 20 minutes at 30° C., this mixture imparts to the hair, after rinsing and shampooing, a bluish grey colouration.

EXAMPLE 37

The following dyeing composition is prepared:

| | |
|---|---|
| 1-(2',4'-Diaminophenoxy)-3-dimethylaminopropan-2-ol trihydrochloride monohydrate | 0.35 g |
| Para-aminophenol | 0.109 g |
| Acrylic acid polymer having a molecular weight of 2 to 3 million, sold under the name "CARBOPOL 934" by "GOODRICH CHEMICAL CO" | 3 g |
| Ethanol (96° strength) | 11 g |
| 2-Butoxyethanol | 5 g |
| Trimethylcetylammonium bromide | 2 g |
| Ethylenediaminetetraacetic acid sold under the name "TRILON B" | 0.2 g |
| Ammonia solution (22° Be strength) | 10 g |
| Sodium bisulphite solution (35° Be strength) | 1 g |
| Water qs | 100 g |

The pH of the composition is equal to 9.8.

100 g of hydrogen peroxide of 20 volumes strength are added at the time of use.

When applied for 25 minutes at 28° C. to hair which has been bleached white, this mixture imparts to the hair, after rinsing and shampooing, a pink shade with a golden sheen.

EXAMPLE 38

The following dyeing composition is prepared:

| | |
|---|---|
| 1-(2',4'-Diaminophenoxy)-3-dimethylamino-propan-2-ol trihydrochloride monohydrate | 0.13 g |
| Para-phenylenediamine | 0.08 g |
| Para-aminophenol | 0.16 g |
| Resorcinol | 0.13 g |
| Meta-aminophenol | 0.09 g |
| 2-Methyl-5-N—(β-hydroxyethyl)-aminophenol | 0.1 g |
| 3-N—Methylamino-4-nitrophenoxyethanol | 0.03 g |
| Oleyl alcohol oxyethyleneated with 2 mols of ethylene oxide | 4.5 g |
| Oleyl alcohol oxyethyleneated with 4 mols of | 4.5 g |

| | |
|---|---|
| ethylene oxide | |
| Oleylamine oxyethyleneated with 12 mols of ethylene oxide, sold under the name "ETHOMEEN TO₁₂" by "ARMOUR HESS" | 4.5 g |
| Diethanolamides of copra fatty acids | 9 g |
| Propylene glycol | 4 g |
| 2-Butoxyethanol | 8 g |
| Ethanol (96° strength) | 6 g |
| Pentasodium salt of diethylenetriaminepentaacetic acid, sold under the name "MASQUOL DTPA" | 2 g |
| Hydroquinone | 0.15 g |
| Sodium bisulphite solution (35° Be strength) | 1.3 g |
| Ammonia solution (22° Be strength) | 10 g |
| Water qs | 100 g |

The pH of the composition is equal to 10.

120 g of hydrogen peroxide of 20 volumes strength are added at the time of use.

When applied to 90% naturally white hair for 25 minutes at 28° C., this mixture imparts to the hair, after rinsing and shampooing, a hazel colouration.

EXAMPLE 39

The following dyeing composition is prepared:

| | |
|---|---|
| 1-(2',4'-Diaminophenoxy)-3-dimethylaminopropan-2-ol trihydrochloride monohydrate | 0.25 g |
| Para-phenylenediamine | 0.4 g |
| Para-aminophenol | 0.6 g |
| 2-Methylresorcinol | 0.4 g |
| 2-Methyl-5-N—(β-hydroxyethyl)-aminophenol | 0.25 g |
| 2-Amino-3-nitrophenol | 0.2 g |
| Nonylphenol oxyethyleneated with 4 mols of ethylene oxide, sold under the name "REMCOPAL 334" by "GERLAND" | 21 g |
| Nonylphenol oxyethyleneated with 9 mols of ethylene oxide, sold under the name "REMCOPAL 349" by "GERLAND" | 24 g |
| Oleic acid | 4 g |
| 2-Butoxyethanol | 3 g |
| Ethanol (96° strength) | 10 g |
| Pentasodium salt of diethylenetriaminepentaacetic acid, sold under the name "MASQUOL DTPA" | 2.5 g |
| Sodium bisulphite solution (35° Be strength) | 1 g |
| Ammonia solution (22° Be strength) | 10 g |
| Water qs | 100 g |

The pH of the composition is equal to 10.1.

120 g of hydrogen peroxide of 20 volumes strength are added at the time of use.

When applied for 15 minutes at 30° C. to hair which has been bleached straw yellow, this mixture imparts to the hair, after rinsing and shampooing, a coppery chestnut colouration.

EXAMPLE 40

The following dyeing composition is prepared:

| | |
|---|---|
| 1-(2',4'-Diaminophenoxy)-3-dimethylamino-propan-2-ol trihydrochloride monohydrate | 0.075 g |
| Para-phenylenediamine | 0.20 g |
| N,N—Di-(β-hydroxyethyl)-para-phenylenediamine dihydrochloride | 0.09 g |
| N—Methyl-para-aminophenol sulphate | 0.115 g |
| 2-Methylresorcinol | 0.3 g |
| Meta-aminophenol | 0.085 g |
| 1-Amino-2-nitro-4-N—(β-hydroxyethyl)-amino-5-methylbenzene | 0.18 g |
| 3-Nitro-4-N—(β-aminoethyl)-aminophenoxyethanol | 0.15 g |
| Cetyl/stearyl alcohol sold under the name "ALFOL C16/18E" by "CONDEA" | 8 g |
| Sodium cetyl/stearyl-sulphate sold under the name "LANETTE WAX E" by "HENKEL" | 0.5 g |
| Oxyethyleneated castor oil sold under the name "CEMULSOL B" by "RHONE POULENC" | 1 g |
| Oleic diethanolamide | 1.5 g |
| Pentasodium salt of diethylenetriaminiepentaacetic acid, sold under the name "MASQUOL DTPA" | 2.5 g |
| Mercaptosuccinic acid | 0.3 g |
| Ammonia solution (22° Be strength) | 11 g |
| Water qs | 100 g |

The pH of the composition is equal to 9.3.

100 g of hydrogen peroxide of 20 volumes strength are added at the time of use.

When applied to 90% naturally white hair for 25 minutes at 25° C., this mixture imparts to the hair, after rinsing and shampooing, a deep chestnut colouration with a coppery sheen.

EXAMPLE 41

The following dyeing composition is prepared:

| | |
|---|---|
| 2-Hydroxy-3-(2',4'-diaminophenoxy)-propyl-trimethylammonium chloride dihydrochloride hemihydrate | 0.1 g |
| Para-toluylenediamine dihydrochloride | 0.085 g |
| Para-aminophenol | 0.155 g |
| Resorcinol | 0.08 g |
| Meta-aminophenol | 0.09 g |
| 2-Methyl-5-N—(β-hydroxyethyl)-aminophenol | 0.1 g |
| Acrylic acid polymer having a molecular weight of 2 to 3 million, sold under the name "CARBOPOL 934" by "GOODRICH CHEMICAL CO" | 1.5 g |
| Ethanol (96° strength) | 11 g |
| 2-Butoxyethanol | 5 g |
| Trimethylcetylammonium bromide | 1 g |
| Ethylenediaminetetraacetic acid sold under the name "TRILON B" | 0.1 g |
| Ammonia solution (22° Be strength) | 10 g |
| Thioglycolic acid | 0.2 g |
| Water qs | 100 g |

The pH of the composition is equal to 9.9.

100 g of hydrogen peroxide of 20 volumes strength are added at the time of use.

When applied to 90% naturally white hair for 25 minutes at 28° C., this mixture imparts to the hair, after rinsing and shampooing, a hazel colouration.

It is clearly understood that the embodiments described above in no way imply a limitation and can form the subject of any desirable modifications without thereby exceeding the scope of the invention.

We claim:

1. An aqueous hair dye composition comprising a hair dyeing amount of a hair dye compound selected from the group consisting of (1) a compound of the formula

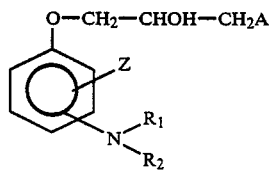

wherein Z is selected from the group consisting of NO₂ and NH₂,

A is selected from the group consisting of NY and

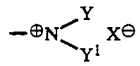

wherein Y represents two identical or different lower alkyl or lower hydroxyalkyl groups wherein each alkyl has 1-4 carbon atoms, or said two Y groups together with the nitrogen atom to which they are attached form a morpholino or piperidino ring, or when A is NY, each Y group can represent hydrogen or one Y group can represent hydrogen and the other Y group can represent alkyl or hydroxyalkyl, wherein the alkyl or each has 1-4 carbon atoms, $Y^1$ represents lower alkyl having 1-4 carbon atoms and X represents halogen, and $R_1$ and $R_2$ each independently represent hydrogen, lower alkyl having 1-4 carbon atoms or hydroxyalkyl having 1-4 carbon atoms, with the proviso that when Z represents $NH_2$ in a meta position relative to $-NR_1R_2$ and A represents NY and Z is in the 4 position on the benzene nucleus and $-NR_1R_2$ is in the 2-position on the benzene nucleus, and $R_1$ and $R_2$ both represent hydrogen then (a) one of the two Y groups in NY is not ethyl if the other Y group is hydrogen and (b) the two Y groups in NY do not form together with the nitrogen atom to which they are attached a morpholino or piperidino ring, and (2) an acid salt of the compound in (1), said hair dye compound being present in an amount ranging from 0.001 to 4 percent by weight based on the total weight of said composition.

2. The hair dye composition of claim 1 wherein Z in said hair dye compound is $NH_2$ in the meta position relative to the $-NR_1R_2$ group and wherein said composition also contains an oxidation base selected from the group consisting of (a) a paraphenylenediamine selected from the group consisting of (i) a paraphenylenediamine having the formula

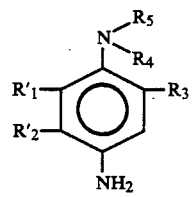

wherein $R'_1$, $R'_2$ and $R_3$ each independently are selected from the group consisting of hydrogen, alkyl having 1-4 carbon atoms, alkoxy having 1-2 carbon atoms and halogen, $R_4$ and $R_5$ each independently are selected from the group consisting of hydrogen, alkyl containing 1-4 carbon atoms, hydroxyalkyl containing 1-4 carbon atoms, alkoxyalkyl wherein the alkoxy moiety contains 1-2 carbon atoms and the alkyl moiety contains 1-4 carbon atoms, carbamylalkyl wherein the alkyl moiety contains 1-4 carbon atoms, alkylsulphonamidoalkyl wherein the alkyl moieties contain 1-4 carbon atoms, acetylaminoalkyl wherein the alkyl moiety contains 1-4 carbon atoms, ureidoalkyl wherein the alkyl moiety contains 1-4 carbon atoms, carbethoxyamino alkyl wherein the alkyl moiety contains 1-4 carbon atoms, aminoalkyl wherein the alkyl moiety contains 1-4 carbon atoms, monoalkylaminoalkyl wherein the alkyl moieties contain 1-4 carbon atoms, piperidinoalkyl wherein the alkyl moiety contains 1-4 carbon atoms, morpholinoalkyl wherein the alkyl moiety contains 1-4 carbon atoms and dialkylaminoalkyl wherein the alkyl moieties contain 1-4 carbon atoms, or $R_4$ and $R_5$ together with the nitrogen atom to which they are attached form a piperdino or morpholino group, with the proviso that $R'_1$ and $R_3$ represent hydrogen when $R_4$ and $R_5$ do not represent hydrogen, and (ii) the acid salt of (i), (b) a para-aminophenol selected from the group consisting of (i') a para-aminophenol having the formula

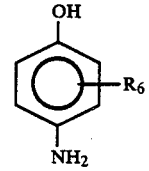

wherein $R_6$ represents a member selected from the group consisting of hydrogen, alkyl having 1-4 carbon atoms and halogen, and (ii') the acid salt of (i') and (c) a heterocyclic base selected from the group consisting of 2,5-diaminopyridine, 3-methyl-7-aminobenzomorpholine and 5-aminoindole, said hair dye compound being present in an amount ranging from 0.001 to 2.5 percent by weight based on the total weight of said composition.

3. The hair dye composition of claim 2 which also contains a coupler selected from the group consisting of resorcinol, pyrocatechol, 2-methyl resorcinol, 2-ethyl resorcinol, meta-aminophenol, 2-methyl-5-aminophenol, 2-methyl-5-N-(β-hydroxyethyl)aminophenol, 6-hydroxybenzomorpholine, 2-6-dimethyl-3-acetylaminophenol, 2-methyl-5-carbethoxyaminophenol, 2-methoxy-5-carbethoxyaminophenol, 2-methyl-5-ureidophenol, 2,4-diaminophenoxyethanol, 2,4-diaminoanisole, 2,6-dimethyl-meta-phenylenediamine, 2-amino-4-N-methylaminophenoxyethanol, 2,4-diaminophenyl-β-methoxyethyl ether, 2,4-diaminophenyl-β-mesylaminoethyl ether, 2-N-carbamylmethylamino-4-amino anisole, 3-amino-4-methoxyphenol, α-naphthol, 2,6-diaminopyridine, 3-5-diamino-2,6-dimethoxypyridine, 1-phenyl-3-methylpyrazol-5-one and 2-amino-4-N-(β-hydroxyethyl)aminophenyl-β-hydroxypropyl ether.

4. The hair dye composition of claim 1 which also includes a compound selected from the group consisting of ortho-diphenol, ortho-phenylene diamines and ortho-aminophenols.

5. The hair dye composition of claim 1 which also includes a member selected from the group consisting of 2,6-diaminohydroquinone dihydrochloride, 2,6-diamino-4-N,N-bis-(ethyl)-aminophenol trihydrochloride, 2,4-diaminophenyl dihydrochloride, 1,2,4-trihydroxybenzene, 2,3,5, trihydroxytoluene and 4-methoxy-2-amino-N-(β-hydroxyethyl)-aniline.

6. The hair dye composition of claim 1 which also includes a quinone dyestuff selected from the group consisting of 2-hydroxy-1,4-naphthoquinone, 5-hydroxy-1,4-naphthoquinone and 2-[4'-(N,N-dihydroxyethylamino)-anilino]-5-N'-(β-hydroxyethyl)amino-1,4-benzoquinone.

7. The hair dye composition of claim 1 which also includes an azo dye, an anthraquinone dye, a nitrobenzene dye, an indoaniline, an indophenol, an indamine or a leuco derivative of said indoaniline, indophenol and indamine.

8. The hair dye composition of claim 1 having a pH of 5 to 11.5.

9. The hair dye composition of claim 1 in the form of a liquid, cream, gel or aerosol.

10. A process for dyeing hair comprising applying to said hair the composition of claim 1 in an amount effective to dye said hair, leaving said composition in contact with said hair for a period of time from 10 to 45 minutes, rinsing said hair and drying said hair.

11. The process of claim 10 wherein said composition also contains an oxidation base and as an oxidizing agent, hydrogen peroxide, urea peroxide or ammonium persulfate, said oxidizing agent being added to said composition at the time of use.

* * * * *